US008067565B2

(12) United States Patent
Kinney et al.

(10) Patent No.: US 8,067,565 B2
(45) Date of Patent: Nov. 29, 2011

(54) DENGUE SEROTYPE 1 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Centers For Disease Control and Prevention, Atlanta, GA (US)

( * ) Notice: Subject to any disclaimer, the term of this patent is extended or adjusted under 35 U.S.C. 154(b) by 149 days.

(21) Appl. No.: 12/633,411

(22) Filed: Dec. 8, 2009

(65) Prior Publication Data

US 2010/0137571 A1 Jun. 3, 2010

Related U.S. Application Data

(62) Division of application No. 11/449,876, filed on Jun. 9, 2006, now Pat. No. 7,641,907.

(60) Provisional application No. 60/691,243, filed on Jun. 17, 2005.

(51) Int. Cl.
*A61K 39/12* (2006.01)

(52) U.S. Cl. .................................. 536/23.72; 424/218.1

(58) Field of Classification Search ........................ None
See application file for complete search history.

(56) References Cited

FOREIGN PATENT DOCUMENTS

WO WO 01/60847 A2 * 8/2001

* cited by examiner

*Primary Examiner* — Stacy B. Chen

(74) *Attorney, Agent, or Firm* — B. Aaron Schulman, Esq.; Terry L. Wright, Esq.; Stites & Harbison, PLLC

(57) ABSTRACT

The invention relates to live attenuated VDV1 (VERO-Derived Dengue serotype 1 virus) strains which have been derived from the wild-type dengue-1 strain 16007 by passaging on PDK and sanitization on Vero cells and nucleic acids thereof. The invention further relates to a vaccine composition which comprises a VDV1 strain.

4 Claims, 5 Drawing Sheets

```
Den1-16007/PDK11    LAV-1
                    from : Mahidol university
                    titer= 4,6 log TCID₅₀/5ml

V100                PDK11 + Amplification on Vero cells
                    titer= 6,9 log TCID₅₀/5ml

TV100               Transfection on Vero cells
                    titer= 6,95 log TCID₅₀/5ml

TV110
TV120               Plaque Purification 1

TV111
TV112               Plaque Purification 2
TV121

TV111
TV112               Amplification 1
TV121
          Titers:   TV111 : 6,85 log TCID₅₀/5ml
                    TV112 : 6,80 log TCID₅₀/5ml
                    TV121 : 6,80 log TCID₅₀/5ml

TV111 PM            Amplification 2
```

DENGUE SEROTYPE 1 ATTENUATED STRAIN

CROSS-REFERENCE TO RELATED APPLICATIONS

The present application is a divisional of U.S. application Ser. No. 11/449,876, filed Jun. 9, 2006, now U.S. Pat. No. 7,641,907, which claims the benefit of U.S. provisional application 60/691,243, filed on Jun. 17, 2005, incorporated herein by reference.

The invention relates to new live attenuated VDV1 (VERO-Derived Dengue serotype 1 virus) strains which are derived from the wild-type dengue-1 strain 16007 by passaging on PDK and Vero cells, and sanitization. The invention further relates to a vaccine composition which comprises such VDV1 strain.

Dengue diseases are caused by four closely related, but antigenically distinct, virus serologic types (Gubler, 1988; Kautner et al., 1997; Rigau-Pérez et al., 1998; Vaughn et al., 1997), of the genus Flavivirus (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalised DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanisation particularly in association with poverty, increased air travel, lack of effective mosquito control, and the deterioration of sanitary and public health infrastructure (Gubler, 2002). The awareness of dengue in travellers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and Aedes aegypti, a domestic, day-biting mosquito that prefers to feed on humans. Human infection is initiated by the injection of virus during blood feeding by an infected Aedes aegypti mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13=LAV1), serotype 2 (strain 16681, passage 53), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The complete sequence of the Dengue 1 Live-Attenuated Virus strain (LAV1) was established by R. Kinney et al. (CDC, Fort Collins). Sequence differences between parent DEN-1 strain 16007 (SEQ ID No.2) and LAV1 (SEQ ID No.3) strain are described in Table 1. Thus, genetic comparison of the wild-type virus strain 16007 and LAV1 strain showed a set of 14 point mutations which could be linked to LAV1 attenuation.

TABLE 1

DEN-1 16007 and DEN-1 16007/PDK13 (LAV1) Sequence Differences

| Coordinates | | LAV1 (DEN-1 16007/PDK13) | | 16007 | |
|---|---|---|---|---|---|
| Gene-aa | position | Nt | aa | nt | aa |
| **E-130** | **Nt-1323** | **C** | **Ala** | **T** | **Val** |
| **E-203** | **Nt-1541** | **A** | **Lys** | **G** | **Glu** |
| | **Nt-1543** | **G** | | **A** | |
| **E-204** | **Nt-1545** | **A** | **Lys** | **G** | **Arg** |
| E-211 | Nt-1567 | G | Gln | A | Gln |
| **E-225** | **Nt-1608** | **T** | **Leu** | **C** | **Ser** |
| **E-477** | **Nt-2363** | **G** | **Val** | **A** | **Met** |
| NS1-92 | Nt-2695 | C | Asp | T | Asp |
| NS1-121 | Nt-2782 | T | Ala | C | Ala |
| **NS3-182** | **Nt-5063** | **A** | **Lys** | **G** | **Glu** |
| **NS3-510** | **Nt-6048** | **T** | **Phe** | **A** | **Tyr** |
| **NS4A-144** | **Nt-6806** | **G** | **Val** | **A** | **Met** |
| NS4B-168 | Nt-7330 | G | Gln | A | Gln |
| NS5-624 | Nt-9445 | T | Ser | C | Ser |

Nucleotide changes modifying the corresponding codon are indicated in bold.

The LAV1 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV1 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By first transferring the LAV1 vaccine strain from PDK to VERO cells and then transfecting Vero cells with the purified genomic RNA of LAV1, followed by two successive steps of virus plaque purification the Applicant produced a new Vero-Derived serotype 1 virus (VDV1).

This new VDV1 strain which has been thus derived by transfer to VERO cells and biological cloning differs from the LAV1 strain by sequence, an homogenous plaque size and temperature sensitivity but importantly has conserved some phenotypic and genotypic features of the LAV1 such as e.g. attenuation spots, small plaque phenotype, growth restriction at high temperature, and has conserved the immunogenic features of the LAV1 strains. These features make this new strain a valuable vaccine candidate for prophylactic immunization in humans.

Definitions

"Dengue viruses" are positive-sense, single-stranded RNA viruses belonging to the Flavivirus genus of the flaviridae family. In the case of dengue serotype 1 (DEN-1) strain 16007, the entire sequence is 10735 nucleotides long (SEQ ID No.2). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-1 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 1 (DEN-1) strain 16007 by passages, e.g. 10, 11, 12 or 13 passages, in Primary Dog Kidney (PDK) Cells. For instance "LAV1/PDK13" is the attenuated strain established after 13 passages of strain 16007 in PDK cells (also named DEN-1 16007/PDK13). LAV1/PDK13 nucleotide sequence is shown in SEQ ID No.3.

"VDV1" is meant a LAV obtainable by the sanitization process disclosed in the present application. A VDV1 is thus a biological clone (homogeneous) VERO-adapted Dengue serotype 1 virus capable of inducing a specific humoral immune response including neutralizing antibodies in primate especially in humans. The VDV1 strains of the invention can be easily reconstructed starting directly from the here disclosed VDV1 sequences. The induction of a specific humoral immune response can be easily determined by an ELISA assay. The presence of neutralising antibody in the serum of a vaccinee is evaluated by the plaque reduction neutralization test as described in section 4.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitutions of one or more nucleotides. In the context of the instant application, mutations identified in dengue-1 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions are designated for instant by "S9G", which means that Ser in position 9 is replaced by Gly.

VERO-Derived Dengue Serotype 1 Viruses (VDV1)

The composition of the previously developed dengue-1 vaccine candidate LAV1 was improved by a sanitization process.

The VERO-Derived Dengue serotype 1 viruses (VDV1) disclosed herein use the DEN-1 16007 virus attenuated by serial passages on PDK cells. VDV1 contains the whole genomic sequence of the live-attenuated DEN-1 virus, and bears the same spots which have been linked to attenuation as the original LAV1 strain that was tested in humans.

Sanitization of the LAV1 vaccine candidate was performed by removing proteins and introducing only purified viral genomic material into Vero cells. More specifically, sanitization of the strain was performed in 2 steps:

1) Amplification of DEN16007/PDK11 (LAV1/PDK11) on Vero cells, at 32° C.

2) Purification and transfection of viral RNA into Vero cells.

Step 1 has been carried out by one passage of LAV1/PDK11 on Vero cells. For that purpose, Vero cells were infected with LAV1/PDK11 at a moi of 0.01 and incubated at 32° C. for 5 days.

For step 2, advantage was taken of the fact that the viral genome is an infectious RNA, which means that it is able, when introduced into a cell, to reconstitute a complete infectious virus. The second purification and transfection step thus comprised the steps consisting of:

a) extracting and purifying viral RNA from plaque-purified viruses;

b) advantageously associating of the purified RNA with cationic lipids;

c) transfecting Vero cell, in particular Vero cell LS10;

d) recovering of the neo-synthesized viruses; and e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5+/−0.2 as determined by a pH meter at RT. Before use, the lyophilised product is mixed with a pharmaceutically diluent or excipient such as a sterile NaCl 4% o solution to reconstitute a liquid immunogenic composition or vaccine.

Sequencing, at attenuation-specific loci, of virus recovered after transfection, did not reveal any mutation, compared to the LAV1/PDK13 strain. The biologically cloned VDV1 virus exhibits a homogenous plaque phenotype and a remarkable genetic stability with regard to its LAV1 parent as it can be deduced especially from the conservation of the attenuation genotype.

VDV1 strain was sequenced and compared with the serotype 1 Dengue Live Attenuated Virus (LAV1/PDK13) strain sequence (SEQ ID No 3). A set of 3 nucleotide differences was found with regard to the reference LAV1 sequence. One of them is silent at the amino acid level (position 2719). The two others (positions 5962 and 7947) are located in non-structural peptides coding sequences (NS3-481 and NS5-125, respectively). None of these differences corresponds to any of the LAV1 attenuation positions.

The invention thus provides for live attenuated dengue-1 virus strains that have been obtained from the wild type virus DEN-1 16007 attenuated by serial passages on PDK cells and then by passage and sanitization on VERO cells. In particular the attenuated strains of the invention comprise at least the identified sequence mutations (non-silent and optionally silent) relative to the nucleotide sequence or polyprotein sequence of the wild-type DEN-1 16007 and LAV1/PDK13 strains.

Accordingly, the invention relates to an isolated live attenuated dengue-1 virus strain which comprises, or consists of, the sequence of LAV1/PDK13 strain (SEQ ID No.3) wherein at least nucleotides at positions 5962 and 7947, and optionally 2719, are mutated, with the proviso that the following nucleotides are not mutated: 1323, 1541, 1543, 1545, 1567, 1608, 2363, 2695, 2782, 5063, 6048, 6806, 7330, and 9445. Preferably, the mutations are substitutions. Preferably, the nucleotide at position 5962 is A, the nucleotide at position 7947 is G. Still preferably, the isolated strain according to the invention contains sequence SEQ ID No.3 which comprises the mutations 2719 G>A, 5962 C>A, and 7947 A>G.

Hence, a live attenuated dengue-1 virus strain according to the invention comprises the sequence of wild-type dengue-1 strain 16007 (SEQ ID No.2) wherein said sequence comprises at least the mutations 1323 T>C, 1541 G>A, 1543 A>G, 1545 G>A, 1567 A>G, 1608 C>T, 2363 A>G, 2695 T>C, 2782 C>T, 5063 G>A , 5962 C>A, 6048 A>T, 6806 A>G, 7330 A>G, 7947 A>G, and 9445 C>T. Preferably, a live attenuated strain according to the invention further comprises the mutation 2719 G>A by reference to the nucleotide sequence of wild-type strain 16007 (SEQ ID No.2).

The live attenuated dengue-1 virus strains according to the invention encompass variant strains that comprise a sequence SEQ ID No.3 mutated in positions 5962 and 7947, as defined above, and that further comprise a substitution of one or more nucleotides in a given codon position that results in no alteration in the amino acid encoded at that position.

Advantageously, the live attenuated dengue-1 virus strain according to the invention comprises a sequence which differs by a limited number of mutations, e.g. no more than 5, still preferably no more than 2, from SEQ ID No.1.

Preferably, the genomic sequence of a dengue-1 virus strain according to the invention consists of the nucleotide sequence SEQ ID No.1.

The invention also relates to live attenuated dengue-1 strains that may be derived from the VDV1 strain of sequence SEQ ID No.1 by further passages on cells, in particular Vero cells.

The invention also relates to an isolated nucleic acid which comprises, or consists of, the DNA sequence SEQ ID No.1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No.1 is meant a sequence SEQ ID No.1 wherein deoxythymidines have been replaced by uridines. As SEQ ID No.1 constitutes VDV1 cDNA sequence, the equivalent RNA sequence thus corresponds to the positive strand RNA of VDV1.

The invention further relates to the polyprotein of sequence SEQ ID No.41 and to fragments thereof. SEQ ID No.41 is the sequence of the polyprotein encoded by SEQ ID No.1

A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No.41 comprise at least a lysine at position 481 of NS3 protein (position 1956 of SEQ ID No.41), and/or an arginine at position 125 of NS5 protein (position 2618 of SEQ ID No.41).

According to an embodiment the fragment of the polyprotein encoded by SEQ ID No.1 is or comprises NS3 protein and/or NS5 protein.

Immunogenic and Vaccine Compositions

The invention also relates to an immunogenic composition, suitable to be used as a vaccine, which comprises a VDV1 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits a specific immune response and/or confers protection against Dengue-1 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV1 according to the invention in combination with at least a live attenuated dengue virus selected from the group consisting of serotype 2, serotype 3, and serotype 4.

Preferably, the immunogenic or vaccine composition may be a tetravalent dengue vaccine composition, i.e. a vaccine composition that comprises a VDV1 according to the invention in combination with a live attenuated dengue-2 virus strain, a live attenuated dengue-3 virus strain and a live attenuated dengue-4 virus strain.

Live attenuated dengue-2, dengue-3 and dengue-4 virus strains have been described previously. Reference may be made to the live-attenuated vaccines that were developed by Mahidol University by passaging dengue serotype 2 (strain 16681, passage 53; LAV2), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV2 (SEQ ID No.42), LAV3 (SEQ ID No.43), and LAV4 (SEQ ID No.44) are shown in the annexed sequence listing.

Advantageously, a live attenuated dengue-2 strain may correspond to a VDV2 strain which has been obtained from the LAV2 strain developed by Mahidol by a process of sanitization on Vero cells. In particular a live attenuated dengue-2 strain (VDV2) may comprise, and advantageously consists of the sequence SEQ ID No.40.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV1 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of an immunogenic composition or a vaccine according to the invention.

A "host in need thereof" denotes a person at risk for dengue infection, i.e. individuals travelling to regions where dengue virus infection is present, and also inhabitants of those regions.

The route of administration is any conventional route used in the vaccine field. The choice of administration route depends on the formulation that is selected. Preferably, the immunogenic composition or vaccine corresponds to an injectable composition administered via subcutaneous route, advantageously in the deltoid region.

The amount of LAV or VDV in particular VDV1 in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or from $10^3$ to $10^5$ $CCID_{50}$ of LAV or VDV, for instance 4±0.5 $\log_{10}$ $CCID_{50}$ of VDV1 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee, as evaluated by the plaque reduction neutralization test as described in section 4.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples.

FIGURES

Figure 3:
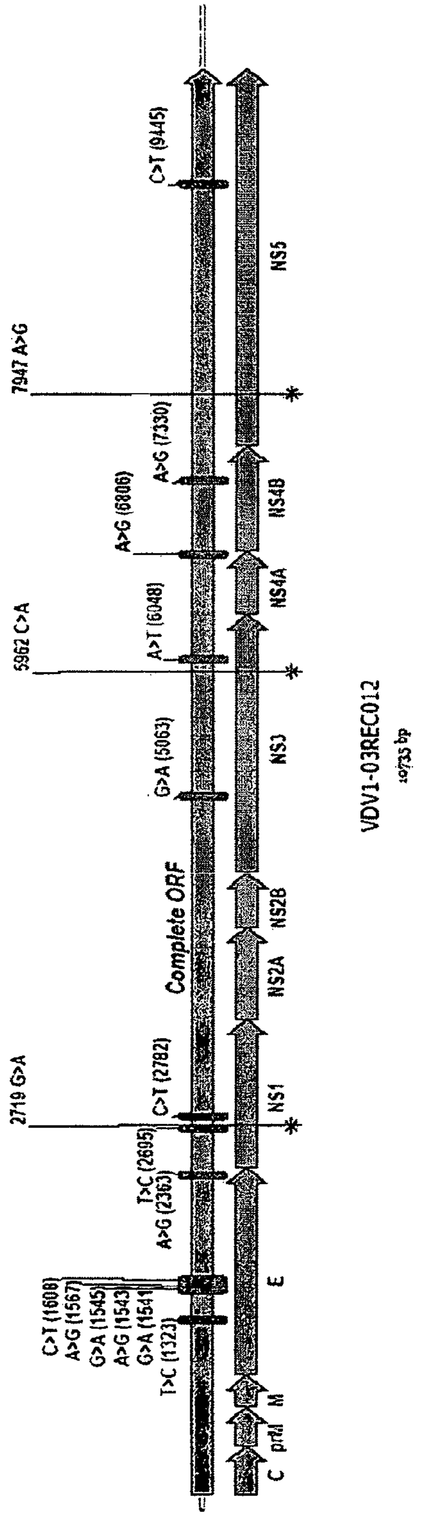

FIG. 3 is a diagrammatic representation of VDV1 genome map. The above arrow is the polyprotein coding sequence. The below arrows represent mature peptides coding sequence. The vertical bars symbolize the nucleotidic variations between wild-type dengue 1 strain16007 and LAV1 strain. The stars designate the nucleotidic variations between LAV1 and VDV1.

Figure 4:
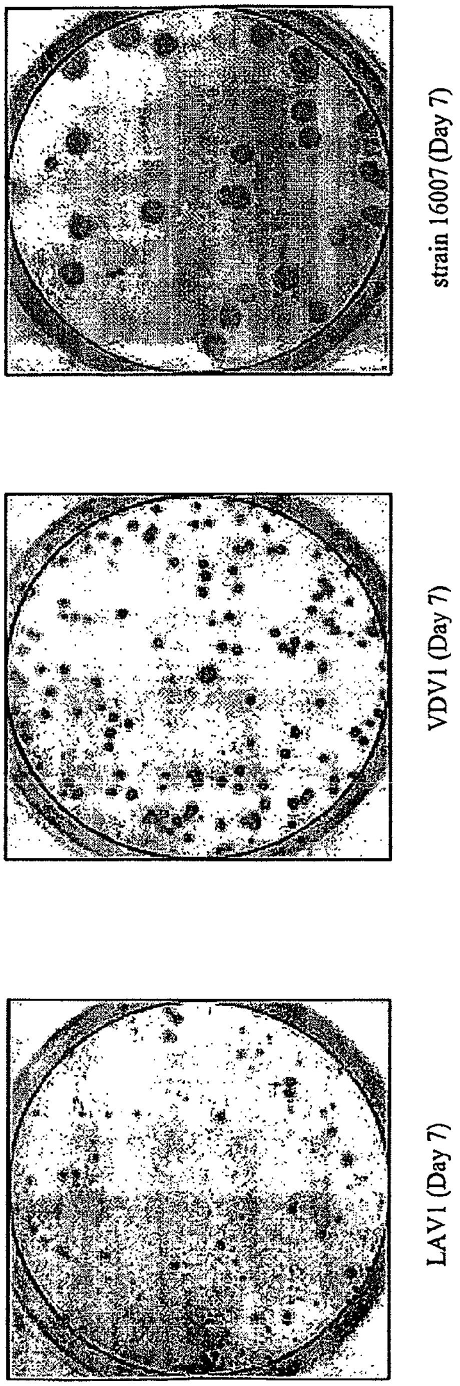

FIG. 4 shows plaque size analysis after 7 days of incubation at 37° C. for dengue-1 viruses LAV1, VDV1, and strain 16007.

Figure 5:
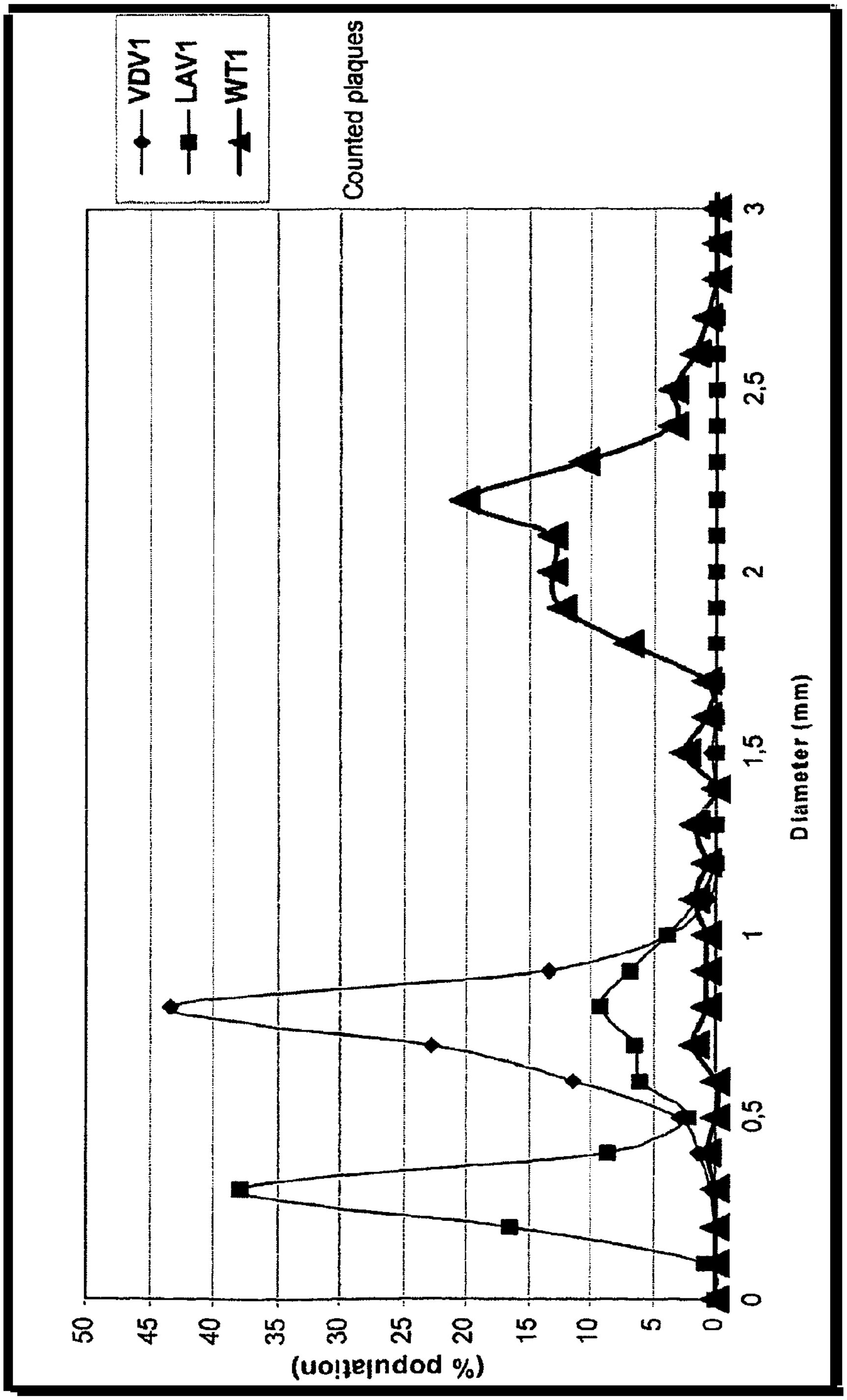

FIG. 5 is a graphic analysis showing plaque size distribution for dengue-1 viruses LAV1, VDV1, and strain 16007.

Figure 6:
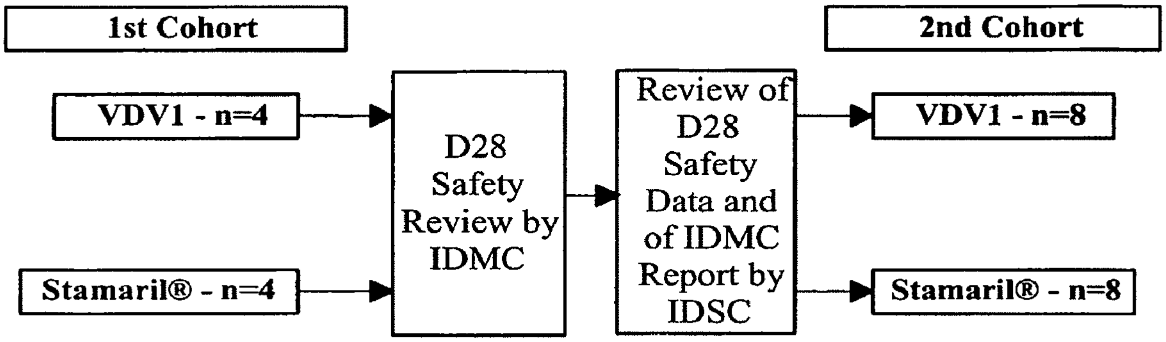

FIG. 6 is a summary of Trial Design for assessment of safety of VDV1 monovalent in healthy flavivirus-naive adults.

EXAMPLES

Example 1

Sanitization 1.1 Viral RNA Purification

It was initialy intended to perform sanitization of LAV1 by purifying and transfecting viral RNA directly extracted from an early seed of the vaccine strain, DEN-16007/PDK10 or DEN-16007/PDK11 (produced by Sanofi Pasteur. Titer: 4.60 $logTCID_{50}$/ml). Eight unsuccessful assays were carried out in that way, with RNA quantities varying from $10^3$ to $10^7$ copies. It was then decided to perform one adaptation passage on Vero cells, before RNA extraction and transfection.

Vero cells (VERO LS10 p142 to145) were infected with a sample of the master seed DEN-1/PDK11, at m.o.i 0.01, and incubated at 32° C. for 5 days. Culture medium was then replaced by infection medium (containing 10 mM $MgSO_4$). Clear cytopathic effects were visible the following day, and presence of viral RNA in culture supernatant was confirmed by RT-PCR. Culture medium was collected at day 8 post-infection, diluted with an equivalent volume of an aqueous buffered solution comprising cryoprotective agents (pH=7.5) and kept frozen at −70° C. until use. This Vero-amplified virus was named DEN-1/V100. Its infectious titer was determined on Vero cells and was of 6.9 $logTCID_{50}$/ml.

The RNA purification and transfection process was performed as follows. DEN-1 V100 suspension was diluted in order to contain at least $3\times10^4$ and up to $3\times10^7$ $TCID_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and βmercaptoethanol (RTL-βmercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free $H_2O$ water. The presence of viral RNA was confirmed by quantitative RT-PCR, using a reference curve established with known quantities of virus, in $TCID_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-$0.5\times10^6$ cells per well in a 6 wells plate) with increasing doses (5 to 20 μl) of lipofectamine. Cells were then incubating 4 to 5 hours at 32° C., 5% $CO_2$, before replacing the medium by fresh culture medium without FCS, and the incubation was continued overnight at 32° C. Toxicity (round, refringent or boating cells, homogeneity of the cell monolayer) was checked regularly for 48 hours, under an inverted microscope. The highest dose of lipofectamine that was not toxic under these conditions was 10 μl and was chosen for RNA transfection.

Four transfections were carried out in parallel, using 1/10 of the purified RNA preparation (corresponding to about $4\times10^5$ $TCID_{50}$). Twelve microliters of viral RNA solution were diluted in 500 μl of OptiMEM medium (GIBCO) containing 10 μl of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells. After 4 hours of incubation at 32° C., transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

Moderate toxic effects were observed 24 hours post-transfection and disappeared on day 3. Typical cytopathic effects (round, refringent cells) were detected 6 to 8 days post-transfection in all transfection assays. Release of virus in the supernatant of these cells was confirmed by qRT-PCR. Culture fluids (3 ml) were collected at day 6 and at day 8 post-transfection, and pooled. The viruses were diluted with 6 ml of an aqueous buffered solution comprising cryoprotective agents (pH=7.5) and frozen until further amplification.

The four viral solutions such obtained after transfection were named TV (for Transfection in Vero cells) 100, TV200, TV300 and TV400, and exhibited similar infectious titers (see below):

TV100: 6.95 log $TCID_{50}$

TV200: 6.80 log $TCID_{50}$

TV300: 6.80 log $TCID_{50}$

TV400: 6.85 log $TCID_{50}$

Of note, transfection efficiency was not significantly increased in samples transfected in presence of tRNA (TV300 and TV400).

1.3 Characterization of Viruses Recovered After Transfection

Plaques sizes of DEN1-V100 and TV100 to 400 were determined. Briefly, Vero cells were plated at a density of 1.000.000 cells/$cm^2$ in culture medium containing 4% of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% CQ in Mimimal Eagle Medium (MEM) containing 1.26% methylcellulose and 10% FBS. After 11 days of incubation, plates were fixed 20 minutes in cold acetone at −20° C. and revealed by immuno-coloration with a flavivirus-specific mAb, diluted at 2.5 μg/ml. Viral plaques were measured using an image analysis software (Saisam/Microvision)

As a control, DEN-1 16007 and LAV1 were plated in parallel. The data are presented in Table 1.

TABLE 1

Plaques size of DEN-1 16007, LAV1, V100 (before transfection) and TVX00 (after transfection)

| Step | Virus | Phenotype: Large Plaque | Phenotype: Small Plaque |
|---|---|---|---|
| | DEN1 16007 (wt) | 42 | 0 |
| Master Seed/PDK11 | MS-16007/PDK11 | 0 | 91 |
| Working Seed/PDK12 | WS LST-22 | 0 | 84 |
| Bulk Seed/PDK13 | D1-0010R1 | 0 | 188 |
| VERO amplification | V100 | 0 | 90 |
| Transfected viruses | TV100 | 0 | 115 |
| | TV200 | 1 | 90 |
| | TV300 | 0 | 92 |
| | TV400 | 0 | 107 |

The V100 virus, amplified on Vero cells, exhibits a homogeneous small plaque (SP) phenotype. Plaques are slightly larger than observed in the different samples of LAV1 (2-3 mm diameter instead of <2 mm). This SP phenotype is retained in the viruses recovered after transfection. One large plaque (LP), among 90 virus plated, was detected in TV200 sample. However, this proportion shifted to 10 LP for 82 SP plated after just one amplification passage on VERO cells suggesting that the LP population was dominant.

Of note, sequencing of attenuation-critical positions performed in parallel did not reveal any mutation in transfected viruses, compared to LAV1.

1.4 Plaque-Purifications

A sample of DEN-1/TV100 virus, presenting a homogenous SP phenotype was chosen for plaque-purification. Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mixed extemporaneally with 2% of melted agarose equilibrated at 42° C. The medium was allowed to solidify at room temperature for 30 min; under flow hood, and plates were incubated in inverted position for 10 days at 32° C.-5% $CO_2$. A second layer of the same medium supplemented with 0.01% of neutral red was then added and plates were incubated for an additional night at 32° C. Four wel-isolated small plaques were picked under sterile conditions using a micropipet equipped with a 0.1 ml tip, and transferred into sterile tubes containing 0.2 ml of MEM-4% FCS. The suspension was homogeneized by vortexing, serially diluted in the same medium, and immediately used to infect 6-well plates of Vero cells. The protocol was repeated and a second picking of six SP was done. Each picked plaque was diluted in 1 ml of medium, before amplification on Vero cells, in T25 $cm^2$ flasks. Culture medium was collected at day 6 post-infection, diluted with the same volume of an aqueous buffered solution comprising cryoprotective agent (pH 7.5) and frozen at −70° C. All these steps were performed at 32° C.

Plaque-purified viruses were named DEN-1/TV111, DEN-1/TV112, DEN-1/TV121, DEN-1/TV131, DNE-1/TV132 and DEN-1/TV141, respectively. Infectious titers were determined on Vero cells (see below):

TV111=6.85 $LogCCID_{50}$/ml TV112=6.80 $LogCCID_{50}$/ml

TV121=6.80 $LogCCID_{50}$/ml TV131=6.70 $LogCCID_{50}$/ml

TV132=6.45 $LogCCID_{50}$/ml TV141=5.70 $LogCCID_{50}$/ml

A second amplification on Vero cells was carried out for three clones: TV111, TV112 and TV121.

1.5 Characterization of Cloned Virus

Plaques size of DEN-1/TV111, DEN-1/TV112, DEN-1/TV121, DEN-1/TV131, DEN-1 TV132 and DEN-1/TV141 candidates were determined. Spot-sequencing of specific attenuation loci was also performed and revealed no mutation (Table 2).

TABLE 2

Sequencing at attenuation-specific spots of DEN-1 viruses

| | | E | | | | | | | NS1 | | NS3 | | NS4A | NS4B | NS5 |
|---|---|---|---|---|---|---|---|---|---|---|---|---|---|---|---|
| Step/cell | Virus | 1323 | 1541 | 1543 | 1545 | 1567 | 1608 | 2363 | 2695 | 2782 | 5063 | 6048 | 6806 | 7330 | 9445 |
| Non attenuated/PGMK | DEN-1 16007 | T | G | A | G | A | C | A | T | C | G | A | A | A | C |
| Vaccine/PDK | DEN-1 16007/ PDK-13 | C | A | G | A | G | T | G | C | T | A | T | G | G | T |
| | TV111 | C | A | G | A | G | T | G | C | T | A | T | G | G | T |
| | TV112 | C | A | G | A | G | T | G | C | T | A | T | G | G | T |

TABLE 2-continued

Sequencing at attenuation-specific spots of DEN-1 viruses

| | | E | | | | | | | NS1 | | NS3 | | NS4A | NS4B | NS5 |
|---|---|---|---|---|---|---|---|---|---|---|---|---|---|---|---|
| Step/cell | Virus | 1323 | 1541 | 1543 | 1545 | 1567 | 1608 | 2363 | 2695 | 2782 | 5063 | 6048 | 6806 | 7330 | 9445 |
| 2nd plaque-purification/VERO | TV121 | C | A | G | A | G | T | G | C | T | A | T | G | G | T |
| | TV131 | C | A | G | A | G | T | G | C | T | A | T | G | G | T |
| | TV132 | C | A | G | A | G | T | G | C | T | A | T | G | G | T |
| | TV141 | C | A | G | A | G | T | G | C | T | A | T | G | G | T |
| Pre-master seed/VERO | VDV1 (VERO-6) | C | A | G | A | G | T | G | C | T | A | T | G | G | T |

Nucleotides position are indicated below each gene and referred of DEN-1 16007 strain SEQ ID No 2.

In absence of any other criterion able to differentiate between these clones, TV121 was arbitrarily chosen as pre-master for VDV1.

In conclusion, a total number of 6 passages on VERO cells were carried out to adapt and clone the initial DEN-1 16007/PDK11 attenuated strain. Viral RNA was purified and transfected into qualified VERO cells, in conditions fitting with an industrial application (environmental control, traceability of raw material and experiments, certificate of analysis for animal-derived products). The VERO-adapted strain was cloned by plaque-purification to generate pre-master seed of VDV1 vaccine candidate, at VERO passage number 6.

Contrary to LAV1, VDV1 presents a homogenous small plaque size phenotype. Furthermore, no mutation was identified at attenuation-specific positions. Further characterizations have been performed then by determining bulk VDV1 complete sequence and phenotypic testing.

Example 2

Sequencing

The complete sequence of the virus was generated according to the following strategy. Starting from a VDV1-containing sample, the genomic RNA was extracted and purified, retro-transcribed into cDNA. Then all overlapping PCR amplifications were performed from the cDNA, with addition of the sequencing tags at both ends of each PCR product. All individual sequences were generated in automated devices and analysed. Next step consisted of the genome reconstruction by multiple alignments of all individual sequences. At this point, each unexpected nucleotide change, with regard to the reference sequence, was carefully re-analysed by going back to raw data. Such change was systematically confirmed by another sequence performed from a new PCR product. Once all ambiguities were solved, the sequenced virus genome was completed, and the new molecule was created in Vector NTi database. It can be used for inter genomes analysis, by multiple sequence alignment.

2.1 Materials 2.1.1 Viruses

The viruses to which it is referred here are DEN-1 16007; LAV-1/PDK13; VDV1, the sequences of which are given in the attached sequence listing. The complete genome sequence of these viruses is 10735 nucleotides in length.

2.1.2 Primers

All primers have been designed in Seqweb bioinformatics package (Accelrys), primer design module (Table 3).

TABLE 3 list of RT-PCT and sequencing primers

| Name | Primers sequences | | NtStart | NtEnd | Primer length | RT-PCR length | Overlap |
|---|---|---|---|---|---|---|---|
| D1 01+ | GTTTTCCCAGTCACGACtacgtggaccgacaagaacag | (SEQ ID No. 4) | 12 | 32 | 38 | 897 | -32 |
| D1 01- | AACAGCTATGACCATGggatggagttaccagcatcag | (SEQ ID No. 5) | 928 | 908 | 37 | | 201 |
| D1 02+ | GTTTTCCCAGTCACGACtgaacaccgacgagacaaac | (SEQ ID No. 6) | 688 | 707 | 37 | 892 | |
| D1 02- | AACAGCTATGACCATGaggtccaaggcagtggtaag | (SEQ ID No. 7) | 1598 | 1579 | 36 | | 173 |
| D1 03+ | GTTTTCCCAGTCACGACttggaaatgagaccacagaac | (SEQ ID No. 8) | 1386 | 1406 | 38 | 885 | |
| D1 03- | AACAGCTATGACCATGgaaacaccgctgaacaaaac | (SEQ ID No. 9) | 2289 | 2270 | 36 | | 146 |
| D1 04+ | GTTTTCCCAGTCACGACggttcaagaagggaagcag | (SEQ ID No. 10) | 2106 | 2124 | 36 | 903 | |
| D1 04- | AACAGCTATGACCATGttctatccagtaccccatgtc | (SEQ ID No. 11) | 3028 | 3008 | 37 | | 183 |
| D1 05+ | GTTTTCCCAGTCACGACcagaataccaccttcatcatcg | (SEQ ID No. 12) | 2804 | 2825 | 39 | 868 | |
| D1 05- | AACAGCTATGACCATGttcccatccccatcttgtc | (SEQ ID No. 13) | 3689 | 3671 | 35 | | 232 |
| D1 06+ | GTTTTCCCAGTCACGACggaaatcagaccagtcaaggag | (SEQ ID No. 14) | 3418 | 3439 | 39 | 913 | |
| D1 06- | AACAGCTATGACCATGtgttgtgtgaggcaccagag | (SEQ ID No. 15) | 4349 | 4330 | 36 | | 233 |
| D1 07+ | GTTTTCCCAGTCACGACgcaaaccactaaccatgtttc | (SEQ ID No. 16) | 4077 | 4097 | 38 | 901 | |
| D1 07- | AACAGCTATGACCATGccacttgttgtcaccactc | (SEQ ID No. 17) | 4995 | 4977 | 35 | | 259 |
| D1 08+ | GTTTTCCCAGTCACGACccaagggaagagactggaac | (SEQ ID No. 18) | 4699 | 4718 | 37 | 908 | |
| D1 08- | AACAGCTATGACCATGtcctgatttgatgcttggaac | (SEQ ID No. 19) | 5626 | 5606 | 37 | | 201 |
| D1 09+ | GTTTTCCCAGTCACGACaagcacattttaccgatccag | (SEQ ID No. 20) | 5376 | 5396 | 38 | 900 | |
| D1 09- | AACAGCTATGACCATGgtcgtagtttctttctttctccttc | (SEQ ID No. 21) | 6299 | 6275 | 41 | | 182 |
| D1 10+ | GTTTTCCCAGTCACGACgcaatagacggggaatacag | (SEQ ID No. 22) | 6074 | 6093 | 37 | 809 | |
| D1 10- | AACAGCTATGACCATGatgatggtggttttcagcag | (SEQ ID No. 23) | 6901 | 6882 | 36 | | 138 |
| D1 11+ | GTTTTCCCAGTCACGACgtgttgcttattccagagcc | (SEQ ID No. 24) | 6725 | 6744 | 37 | 877 | |
| D1 11- | AACAGCTATGACCATGgctgtcttttccatttttctcc | (SEQ ID No. 25) | 7622 | 7601 | 38 | | 228 |
| D1 12+ | GTTTTCCCAGTCACGACactttgcacatcacagatcc | (SEQ ID No. 26) | 7354 | 7373 | 37 | 821 | |
| D1 12- | AACAGCTATGACCATGttcgcactagcattcctcc | (SEQ ID No. 27) | 8192 | 8174 | 35 | | 175 |
| D1 13+ | GTTTTCCCAGTCACGACcacctgagaaatgtgacacc | (SEQ ID No. 28) | 7980 | 7999 | 37 | 907 | |
| D1 13- | AACAGCTATGACCATGtttccttgtttatgaagctccc | (SEQ ID No. 29) | 8907 | 8886 | 38 | | 207 |

TABLE 3-continued list of RT-PCT and sequencing primers

| Name | Primers sequences | | NtStart | NtEnd | Primer length | RT-PCR length | Overlap |
|---|---|---|---|---|---|---|---|
| D1 14+ | GTTTTCCCAGTCACGACcaaaagcgaaacgaggcac | (SEQ ID No. 30) | 8661 | 8679 | 36 | 894 | |
| D1 14- | AACAGCTATGACCATGgtttcaccacacagtcatctcc | (SEQ ID No. 31) | 9575 | 9554 | 38 | | 221 |
| D1 15+ | GTTTTCCCAGTCACGACagaccagcgaaaaatggaac | (SEQ ID No. 32) | 9314 | 9333 | 37 | 865 | |
| D1 15- | AACAGCTATGACCATGtcccaatgagccttctcac | (SEQ ID No. 33) | 10196 | 10178 | 35 | | 262 |
| D1 16+ | GTTTTCCCAGTCACGACgctaatgctatctgttcagcc | (SEQ ID No. 34) | 9896 | 9916 | 38 | 812 | |
| D1 16- | AACAGCTATGACCATGtgattcaacagcaccattcc | (SEQ ID No. 35) | 10726 | 10707 | 36 | | -28 |
| D1 16i+ | ccatggaagctgtacgc | (SEQ ID No. 36) | 10480 | 10496 | 17 | | |
| D1 16i- | gagacagcaggatctctgg | (SEQ ID No. 37) | 10671 | 10652 | 19 | | |

2.2 Methods 2.2.1 Viral RNA Purification

From previous experience, a minimal of 1000 $DICC_{50}$ is required to get a positive RT-PCR reaction in the next steps. This means that a minimum virus titer of $10^4$ $DICC_{50}$/mL is necessary. Virus genomic RNA was purified using QIAamp viral RNA mini kit (Qiagen), according to the manufacturer's recommendations. Briefly, a volume of 140 µl from a crude viral sample was incubated in the presence of the lysis solution, and loaded onto a kit column. After washing steps, the purified viral RNA was eluted by 60 µl of sterile nuclease-free water containing 1 µl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 µl of purified RNA, in a final reaction volume of 20 µl. The reaction was initiated by hybridization of the minus strand primers. One RT reaction per PCR was performed (Table 1). The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 1. PCR conditions were the following ones:

| | | |
|---|---|---|
| RT | 2 | µl |
| 10x buffer | 2.5 | µl |
| dNTP mix (10 mM) | 2 | µl |
| Primers | 0.8 | µl each |
| H2O | 16.4 | µl |
| Enzyme | 0.5 | µl |

PCR program

| | | | |
|---|---|---|---|
| Denaturation | 94° C. | 2 min | |
| Denaturation | 94° C. | 15 sec | 40 cycles |
| Hybridization | 55° C. | 30 sec | 40 cycles |
| Elongation | 68° C. | 1 min | 40 cycles |
| Elongation | 68° C. | 5 min | |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.

In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene ReadlR 4200 (Li-Cor).

Sequence reaction

| | |
|---|---|
| DNA | up to 200/250 ng |
| Reaction buffer | 7.2 µl |
| Primers (1-2 pM) | 1.5 µl each |
| Enzyme | 1 µl |
| H2O | up to 20 µl |

PCR program

| | | | |
|---|---|---|---|
| Denaturation | 92° C. | 2 min | |
| Denaturation | 92° C. | 15 sec | 30 cycles |
| Hybridization | 50° C. | 30 sec | 30 cycles |
| Elongation | 70° C. | 1 min | 30 cycles |
| Elongation | 70° C. | 10 sec | |

Addition of 3 µl of denaturating/loading buffer.

Denaturation of samples 3 min at 95° C. and ice cooling just before samples loading.

Sequence electrophoresis

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added tail, i.e. a specific motif which has been added at 5' end of all primers:

```
5' primers:
M13SEQ-GTTTTCCCAGTCACGAC      (SEQ ID No. 38)

3' primers:
M13REV-AACAGCTATGACCATG       (SEQ ID No. 39)
```

M13-SEQ and -REV sequences correspond to universal M13 primers motifs (New England Biolabs references).

For final contig assembly, a quick analysis was performed in Vector NTi, in ContigExpress module (Informax). The LAV1 reference sequence was compared with all individual sequencing results. In such conditions, all results could be aligned at the right place on the complete genome, even when some regions were still missing contig assembly, giving a quick visualization of the overall genome alignment.

2.3.1 Complete VDV1 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV1 reference sequence, thus allowing for a better reconstruction of the genome. Any discrepancy in the sequence with regard to the reference required a confirmation on another independent sequence reaction. The complete sequence of VDV1 is shown in SEQ ID No.1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 4 summarizes the characteristics of each individual sequence reaction, indicating start, end and length. Overlaps between adjacent PCR are also indicated, as well as differences with regard to the reference sequence in the last column.

TABLE 4

Dengue VDV1 individual sequences characteristics

| Name | Start | End | Size | Overlap | Comments |
|---|---|---|---|---|---|
| D1 01+ | 35 | 921 | 886 | 0 | |
| D1 01− | 899 | 33 | 866 | 209 | |
| D1 02+ | 712 | 1596 | 884 | | |
| D1 02− | 1569 | 713 | 856 | 196 | |
| D1 03+ | 1415 | 2277 | 862 | | |
| D1 03− | 2253 | 1400 | 853 | 160 | |
| D1 04+ | 2133 | 3027 | 894 | | 2719 G > A (NS1-100 s) |
| D1 04− | 3000 | 2117 | 883 | 212 | 2719 G > A (NS1-100 s) |
| D1 05+ | 2834 | 3681 | 847 | | |
| D1 05− | 3654 | 2815 | 839 | 247 | |
| D1 06+ | 3451 | 4332 | 881 | | |
| D1 06− | 4325 | 3434 | 891 | 243 | |
| D1 07+ | 4113 | 4987 | 874 | | |
| D1 07− | 4961 | 4089 | 872 | 245 | |
| D1 08+ | 4742 | 5564 | 822 | | |
| D1 08− | 5583 | 4742 | 841 | 183 | |
| D1 09+ | 5400 | 5916 | 516 | | |
| D1 09− | 6274 | 5758 | 516 | 197 | 5962 C > A (NS3-481 N > K); 2 sequences |
| D1 10+ | 6114 | 6868 | 754 | | |
| D1 10− | 6883 | 6077 | 786 | 135 | |
| D1 11+ | 6761 | 7504 | 743 | | |
| D1 11− | 7597 | 6733 | 864 | 217 | |
| D1 12+ | 7381 | 8034 | 653 | | 7947 A > G (NS5-125 K > R) |
| D1 12− | 8143 | 7380 | 763 | 141 | 7947 A > G (NS5-125 K > R) |
| D1 13+ | 8003 | 9730 | 727 | | |
| D1 13− | 8857 | 8002 | 855 | 182 | |
| D1 14+ | 8687 | 9472 | 785 | | |
| D1 14− | 9544 | 8675 | 869 | 200 | |
| D1 15+ | 9344 | 10170 | 826 | | |
| D1 15− | 10162 | 9399 | 763 | 253 | |
| D1 16+ | 9917 | 10261 | 344 | | 2 sequences |
| D1 16− | 10706 | 10394 | 312 | 0 | |
| D1 16i+ | 10500 | 10706 | 206 | | |
| D1 16i− | 10649 | 10204 | 455 | | |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). The two extremities of the genome could not be distinguished from all other PCR amplifications. So, in the reconstructed genome (SEQ ID No.1), both genome ends were considered as identical to oligonucleotide sequences (and also identical to the reference). At 5' end, the sequence is that of nucleotides 1 to 34. At 3' end, the sequence is that of nucleotides 10707 to 10735.

2.3.2 Sequence Comparison

Direct sequence comparison between VDV1 strain and LAV1 reference shows a series of 3 nucleotides differences. Table 5 gives the complete list of these positions.

TABLE 5

Sequence comparison between LAV1 and VDV1 strains

| Nucleotides | | | Amino Acids | | | | |
|---|---|---|---|---|---|---|---|
| Nt Position | LAV1 | VDV1 | Region | AA Position | LAV1 | VDV1 | Notes |
| 2719 | G | A | NS1 | 100 | G | G | Silent |
| 5962 | C | A | NS3 | 481 | N | K | |
| 7947 | A | G | NS5 | 125 | K | R | |

Nucleotide change in position 2719 is silent at the amino acid level. The second difference in position 5962 triggers an amino acid change at NS3-481 (asparagine to lysine). Both are hydrophilic, but lysine is positively charged, whereas asparagine is not. The last difference is located in NS5 peptide, substituting lysine to arginine in position NS5-125. Such amino acid substitution is relatively conservative from a chemical point of view, both arginine and lysine residues being hydrophilic and positively charged.

TABLE 6

Search of discrepancies on other Dengue 1 strains

| Nucleotide position on VDV1 strain | Number of strains sharing the same nucleotide |
|---|---|
| 2719 | 24/40 |
| 5962 | 6/40 |
| 7947 | 1/40 |

When performing sequence alignment between all available Genbank serotype 1 Dengue genomic sequences, it appears that most of the identified differences are also present on other strains (see Table 6). One position is unique in the VDV1 strain (position 7947; NS5-125).

Thus, the full genomic sequence of a VDV1 strain of the dengue virus has been established.

Three nucleotide differences have been detected with regard to the parent LAV1 genomic sequence. VDV1 vaccine strain is derived from LAV1, through virus "sanitization" and passage from dog to monkey cells.

Differences between LAV1 and VDV1 can have several origins. First, cloning steps can elect a viral subpopulation that is not 100% identical to the major sequence previously detected in LAV1. Second, LAV1 has been produced on PDK cells, whereas VDV1 has been made on Vero cells. Such passage from dog to monkey cells potentially induces virus changes that reflect adaptation to the new cell line. Third, as for all RNA viruses, the lower viral RNA polymerase fidelity triggers a higher genomic mutation rate than DNA polymerases do.

In term of sequences only 3 differences between LAV1 and VDV1 were observed, corresponding to only 2 amino acids substitutions. All 14 nucleotide positions that have been linked to LAV1 viral attenuation are conserved in VDV1. Furthermore the sequences of master and bulk VDV1 have been compared (Table 7).

Complete VDV1 master seed sequence was aligned with the bulk sequence. No difference between the two sequences was observed, indicating genetic stability across passages.

VDV1 shows a remarkable genetic stability with regard to its LAV1 parent.

Example 3

Characterization

The objective of these studies was to assess whether changes in attenuation markers occurred through passages.

Figure 1:
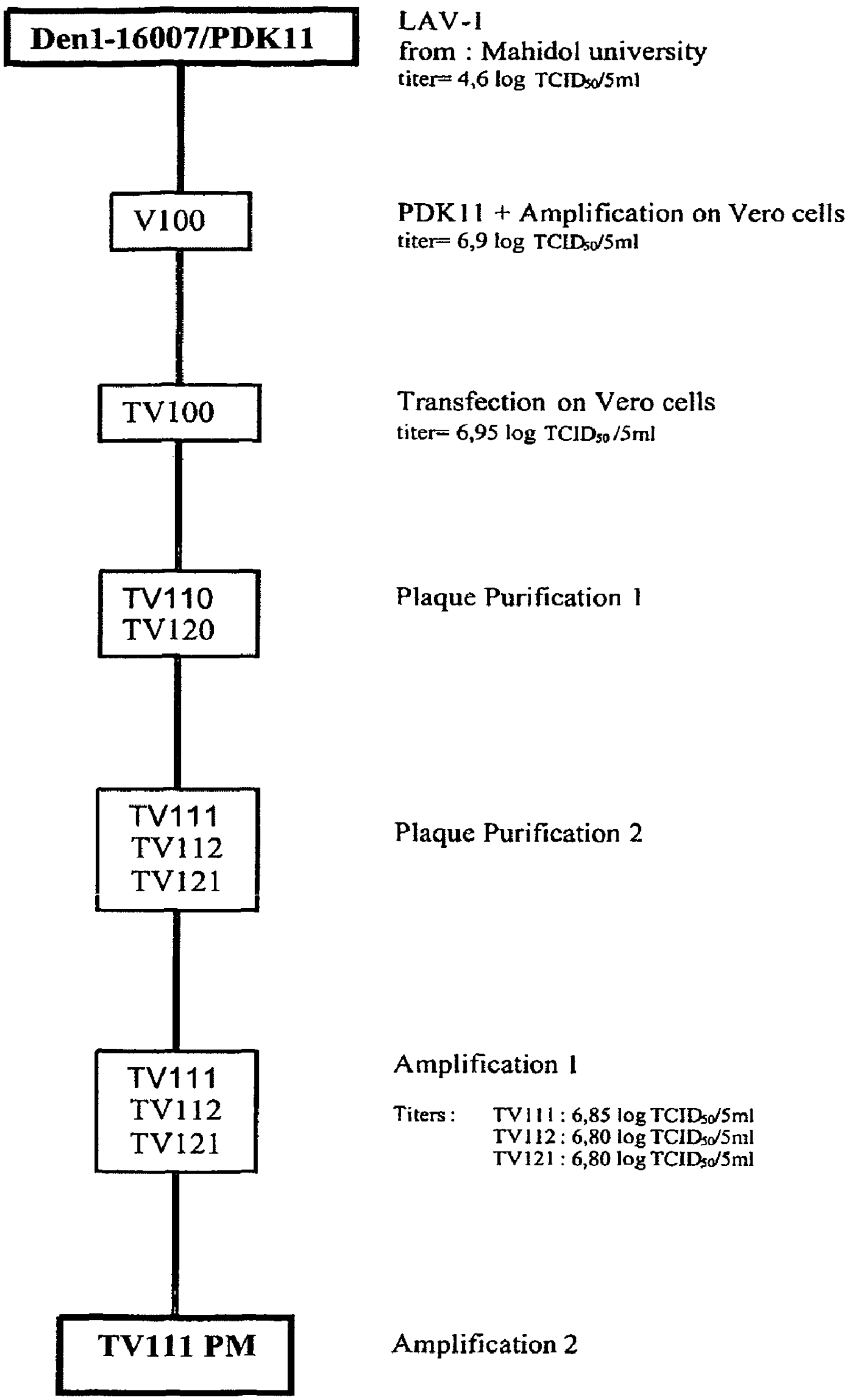
FIG. 1 is a summary of History of VDV1 pre-master seed.
Figure 2:
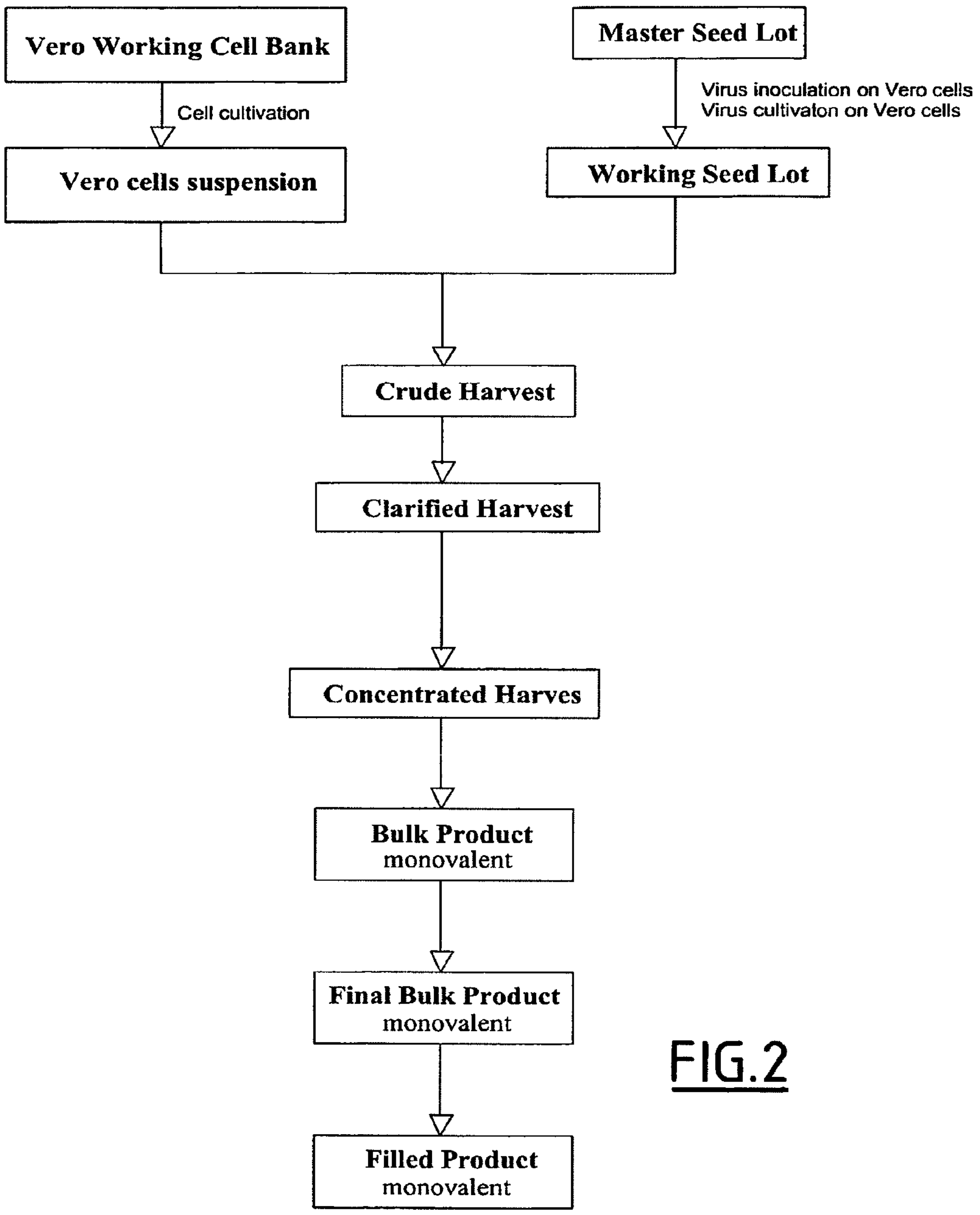
FIG. 2 is a flow chart that summarises the developed manufacturing process that gives rise to the Filled Product (monovalent), "ready to use" doses.

The flow chart shown on FIG. 2 summarises the developed manufacturing process that gives rise to the Filled Product (monovalent), "ready to use" doses Briefly, after 2 successive passages on Vero cells of the Viral Pre-Master Seeds delivered by the Research department, the respective working seeds were obtained. The final virus cultivations were also conducted by infection of a Vero cell suspension. The viruses produced are then harvested. DesoxyRiboNucleic Acid (DNA) was digested according to an enzymatic treatment. Impurities were removed by ultrafiltration. Infectious titers were enhanced by a concentration step. An aqueous buffered solution comprising cryoprotective agents (pH=7.5) is added and this 0.22-μm filtrated mixture is then diluted at the targeted dose within the same solution. The active substance is then filled into glass vials, freeze-dried, and stored before use.

3.1 Phenotypic Markers

The results are shown in Table 8. The validated tests performed for the master seed and the bulk are:

Plaque size: the assay was performed in Vero cells at 37° C. after 7 days of incubation. Sizing of the plaques was performed by Saisam v.5.2.0 (Microvision Instruments) dedicated software, after image capture with a video camera. Two populations (0.3 mm and 0.8 mm) were detected in LAV1. The major population was the smallest. After adaptation to Vero cells and biological cloning, VDV1 plaque size distribution appears homogenous, with more than 98% of the population showing a single peak, centered to 0.8 mm in diameter. These plaques are clearly distinct from plaques obtained with DEN-1 16007 virus (see FIGS. 4 and 5).

Temperature sensitivity: monovalent 1 exhibits clear restricted growth at 39° C. with respect to the non-tempera-

TABLE 7

Dengue 1 nucleotide differences between wild type 16007 strain and attenuated LAV1/PDK13 and VDV1 strains

| Virus | 1323/ E-130 | 1541-3/ E-203 | 1545/ E-204 | 1567/ E-211 | 1608/ E-225 | 2363/ E-477 | 2695/ NS1-92 | 2719/ NS1-100 | 2782/ NS1-121 | 5063/ NS3-182 | 5962/ NS3-481 | 6048/ NS3-510 | 6806/ NS4a-144 | 7330/ NS4b-168 | 7947/ NS5-125 | 9445/ NS5-624 |
|---|---|---|---|---|---|---|---|---|---|---|---|---|---|---|---|---|
| DEN-1 | T | GaA | G | A | C | A | T | G | C | G | C | A | A | A | A | C |
| 16007 | Val | Glu | Arg | Gln | Ser | Met | Asp | Gly | Ala | Glu | Asn | Tyr | Met | Gln | Lys | Ser |
| LAV1/ | C | AaG | A | G | T | G | C | G | T | A | C | T | G | G | A | T |
| PDK13 | Ala | Lys | Lys | Gln | Leu | Val | Asp | Gly | Ala | Lys | Asn | Tyr | Val | Gln | Lys | Ser |
| VDV1 | C | AaG | A | G | T | G | C | A | T | A | A | T | G | G | G | T |
| Master | Ala | Lys | Lys | Gln | Leu | Val | Asp | Gly | Ala | Lys | Lys | Tyr | Val | Gln | Arg | Ser |
| VDV1 | C | AaG | A | G | T | G | C | A | T | A | A | T | G | G | G | T |
| Bulk | Ala | Lys | Lys | Gln | Leu | Val | Asp | Gly | Ala | Lys | Lys | Tyr | Val | Gln | Arg | Ser |

ture sensitive (Ts), wild-type (WT) D1-16007. This was demonstrated both by infectious titer assay and by viral RNA quantification. Master, bulk and passage 18 (10 passages after the bulk passage) of the monovalent 1 seed display 90% or more of titer reduction at 39° C., compared to 37° C.

TABLE 8

Summary of DEN-1 viral phenotypes

| | Temperature sensitivity (Percent titer reduction at 39° C.)$_{Fold\text{-}reduction}$ | | | | | Neurovirulence in newborn Swiss Webster mice | |
|---|---|---|---|---|---|---|---|
| Virus | Score | Day 3 | Day 4 | Day 5 | Day 6 | Mortality$_n$* | AST (S.D.) |
| D1-16007 | – | $62.1_{2.6}$ | $59.3_{2.5}$ | $56.3_{2.3}$ | $(-28.5_{-1.4})$ | $6.25\%_{16}$ | 19.0 (0.0) |
| D1-PDK13 | + | $87.1_{7.8}$ | $91.3_{11.5}$ | $95.5_{22.2}$ | $96.5_{28.6}$ | $0.00\%_{16}$ | n.a. |
| VDV1 MS | + | $97.2_{35.7}$ | $97.7_{43.5}$ | $98.8_{83.3}$ | $99.5_{200.0}$ | $0.00\%_{16}$ | n.a. |

*n: number of animals 3.2 Genotypic Markers

VDV1 vaccine strain can be distinguished from parental strains at the genomic level. Attenuation-specific loci have been identified. These loci are conserved in master and bulk seeds.

Example 4

Immunogenicity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitutes an important parameter to consider. Obviously, immunogenicity is a key parameter when testing vaccines.

Inventors have established minimal/maximal values for viremia and immunogenicity.

Table 9: Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≦3 days | ≦1.5-2 | ≧80 |

pfu: plaque forming unit

PRNT 50: Plaque Reduction Neutralization Titer 50 (titre corresponding to a reduction of 50% of plaque number)

4.1 Material and Methods 4.1.1 Monkey Experiments

Monkey experiments were carried out according to European guidelines regarding animal experiments. Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum separation. To do so, blood was centrifuged for 20 minutes at 4° C., and serum collected and stored at −80° C. until testing in Rich Kinney's laboratory. Shipment to USA was performed in dry ice.

4.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was=10 PFU/ml. For controls stock DEN-16007 PDK-13 (LAV1) vaccine was plated.

4.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN1 16007 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% ($PRNT_{50}$) and 70% ($PRNT_{70}$) endpoint antibody titers. A negative serum result should have a neutralizing antibody titer of <1:10. Sera showing neutralization titers of 320 were retested at dilutions 1:80-1:2560 for determination of endpoint titer.

4.2 Evaluation of VDV Candidates 4.2.1 VDV 1/Pre-Master

Purification/selection of D1 candidate has been conducted as described in example 1. The selected clones (based on phenotypic markers and sequence) have been tested in sanofi pasteur as described in Material and Methods (Marcy I'Etoile animal facility, I15) on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV1: titre: $10^{3,9}$ $DICC_{50}$/ml; lyophilized, resuspended in 0.5 ml of PBS (containing $Ca^{2+}$ and $Mg^{2+}$; $CaCl_2.2H_2O$ 0.133 g/l; $MgCl_2.6H_2O$, 0.1 g/l) and administered in totality.

Premaster VDV1 DEN1-TV111: Titre: $10^{5,9}$ $DICC_{50}$/ml; liquid, diluted at $10^{5,3}$ pfu/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered.

Injection was done by SC route in the arm with a 23G1 needle, at a $10^5$ $DICC_{50}$ dose for VDV1.

The results are as presented in Table 10. Titrations at day 28 were carried out in triplicate ($PRNT_{70}$) or in duplicate ($PRNT_{50}$).

Briefly, responses were rather homogeneous within each group, and some clear tendencies could be identified for each construct. No dramatic differences were found between VDV1 and LAV1: low and late viremia was observed in some LAV1 monkeys. VDV1 looked satisfactory, and in particular presented no viremia.

4.2.2 VDV 1 Bulk

As immunogenicity of the vaccines had been tested at the Premaster stage, a further experiment was designed to test each monovalent at the Bulk stage.

Male *Macaca fascicularis* monkeys were used as before, originating from C.R.P. Le Vallon, Ile Maurice (24 monkeys, mean weight 3.4 kg).

VDV1; Batch: Titre: 8.37 log10 $DICC_{50}$ /ml

Placebo: PBS with $Ca^{2+}$ and $Mg^{2+}$

Vaccines were diluted at $10^{5.3}$ $DICC_{50}$/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered by SC route in the arm with a 23G1 needle, corresponding to a dose of $10^5$ $DICC_{50}$.

Viremia and immunogenicity have been measured as usual in CDC by R Kinney. The results are shown in Table 11.

VDV1 monovalent vaccine induced a significant immune response while viremia was absent. Thus, this monovalent VDV1 fulfilled the success criteria initially defined in monkeys.

TABLE 10

VDV1 PreMaster immunogenicity

AvP monovalent VDV1 (Exp A) DEN Monkey study (F. Mi.DEN003.Si): PRNT and Viremia Results

| | | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day | | | | | | | Day | Day | Day |
| Serum | Group | $PRNT_{70}$ | $PRNT_{50}$ | $PRNT_{70}$ | $PRNT_{50}$ | −15 | Day 2 | Day 3 | Day 4 | Day 5 | Day 6 | Day 7 | 8 | 9 | 10 |
| AD 333 | LAV DEN-1 | <10/<10 | <10 | 320/160/160 | 160/320 | 0 | 0 | 0 | 0 | 0 | 0 | 0 | 0 | 0 | 0 |
| AC 763 | | <10/<10 | <10 | 640/640/640 | 1280/1280 | 0 | 0 | 0 | 0 | 0 | 0 | 0 | 0 | 50 | 150 |
| AD 209 | | <10/<10 | <10 | 320/160/160 | 160/320 | 0 | 0 | 0 | 0 | 0 | 0 | 0 | 0 | 0 | 0 |
| AC 755 | | <10/<10 | <10 | 160/80/160 | 160/160 | 0 | 0 | 0 | 0 | 0 | 0 | 50 | 0 | 0 | 0 |
| AC 775 | VDV DEN-1 | <10/<10 | <10 | 160/80/80 | 160/160 | 0 | 0 | 0 | 0 | 0 | 0 | 0 | 0 | 0 | 0 |
| AC 881 | TV111 | <10/<10 | <10 | 20/10/10 | 20/20 | 0 | 0 | 0 | 0 | 0 | 0 | 0 | 0 | 0 | 0 |
| AD 145 | | <10/<10 | <10 | 320/80/80 | 160/80 | 0 | 0 | 0 | 0 | 0 | 0 | 0 | 0 | 0 | 0 |
| AD 113 | | <10/<10 | <10 | 20/10/10 | 20/20 | 0 | 0 | 0 | 0 | 0 | 0 | 0 | 0 | 0 | 0 |

| Virus | Exp#1 | Exp#2 | Exp#3 |
|---|---|---|---|
| DEN-1 | 112PFU | 45PFU | 101PFU |

TABLE 11

VDV Bulk VDV1 immunogenicity and viremia
Monkey study (F.MI.DEN004.Mk): Monovalent and Tetravalent VDV1

| | | Neutralizing Antibody Titer | | | | Viremia (PFU/ml in Vero cells) | | | | | | | | |
|---|---|---|---|---|---|---|---|---|---|---|---|---|---|---|
| | | Day (−14) | | Day 28 | | Day | | | Day | Day | Day | Day | Day | Day |
| Monkey | Group | $PRNT_{50}$ | $PRNT_{70}$ | $PRNT_{50}$ | $PRNT_{50}$ | −14 | Day 2 | Day 3 | 4 | 5 | 6 | 7 | 8 | 9 |
| AE 484 | VDV DEN-1 | — | — | 14 | 5 | 0 | 0 | 0 | 0 | 0 | 0 | 0 | 0 | 0 |
| AE 627 | | — | — | 8122 | 4558 | 0 | 0 | 0 | 0 | 5 | 0 | 0 | 0 | 0 |
| AF 115 | | — | — | 359 | 202 | 0 | 0 | 0 | 0 | 0 | 0 | 0 | 0 | 0 |
| AF 227 | | — | — | 557 | 367 | 0 | 5 | 0 | 5 | 0 | 0 | 0 | 0 | 0 |
| Geo Mean | Homologous response | — | — | 388 | 203 | | | | | | | | | |
| AE 538 | Placebo | —/—/—/— | —/—/—/— | 2.5/—/2/2 | —/—/—/— | 0 | 0 | 0 | 0 | 0 | 0 | 0 | 0 | 0 |
| AE 548 | | —/—/—/— | —/—/—/— | —/—/1/2 | —/—/—/— | 0 | 0 | 0 | 0 | 0 | 0 | 0 | 0 | 0 |
| AE 556 | | —/—/1.5/2 | —/—/—/— | 1/—/—/— | —/—/—/— | 0 | 0 | 0 | 0 | 0 | 0 | 0 | 0 | 0 |
| AE 572 | | —/—/1.5/5 | —/—/1.5/2 | 5/—/—/2 | —/—/—/— | 0 | 0 | 0 | 0 | 0 | 0 | 0 | 0 | 0 |
| Geo Mean | Response against the four serotypes | —/—/1.2/3 | —/—/1/1 | 2/—/ 1.2/1.6 | —/—/—/— | | | | | | | | | |
| | | D1/D2/D3/ D4 | D1/D2/D3/ D4 | D1/D2/D3/ D4 | D1/D2/D3/ D4 | | | | | | | | | |

4.3 Neurovirulence Tests in Monkeys

For each virus type, 10 cynomolgus monkeys from Mauritius were inoculated with VDV1 master seed by the intracerebral route ($10^{7.23}$ $CCID_{50}$/mL in the thalamus of each hemisphere). At the end of the test, the monkeys were sacrificed and perfused with formaline solution. Tissue samples were taken from the brain of each monkey (medulla oblongata, pons and cerebellum, midbrain, thalamus including the left and the right parts, the left and the right of the cerebral cortex). Sections were cut at a thickness of 8 μm and stained by eosin and gallocyanin.

No histopathological signs of pathogenicity were observed in the monkey brains injected with VDV1 seeds.

Example 5

Safety of Monovalent VDV1 in Healthy, Flavivirus-Naive Adults Aged 18 to 40 Years The aim of this phase 1 trial is to document the safety, viremia, and immunogenicity profiles of monovalent VDV1 at a virus concentration of $10^4$ $CCID_{50}$ compared to Stamaril® (used as control group) in flavivirus-naive adults. Single injections are given, with follow-up at 6 and 12 months. For safety precaution, sequential inclusions are performed in the study.

Enrollment and vaccinations are therefore staggered; a 1st cohort (n=4 per group, total n=12) have been vaccinated. The safety data collected up to Day 28 have been reviewed by an Independent Data Monitoring Committee (IDMC) and by the Royal Adelaide Hospital Investigational Drugs Subcommittee (IDSC) before deciding to proceed with the vaccination of the remaining subjects (n=8per group, total n=16). A schematic representation of the trial design is provided in FIG. 6.

After administration of the vaccine the patient are regularly submitted to various clinical examination and testing. A summary of this follow up is given in table 12 below.

The enrolled population consists of adults aged 18 to 40 years (i.e. the day of the 18th birthday to the day before the 41st birthday) on day of inclusion who are flaviviruses-naïve [persons presenting vaccination against flavivirus diseases (e.g. yellow fever, Japanese encephalitis, dengue fever); or history of flavivirus infection (confirmed either clinically, serologically or microbiologically) or previous residence in or travel to areas with high dengue infection endemicity (whatever the duration), or residence in or travel to North Queensland for 2 weeks or more) were excluded]

TABLE 12

Flow chart for follow up

| | Visit Number | | | | | | | | | | | |
|---|---|---|---|---|---|---|---|---|---|---|---|---|
| | V01 | V02 | V03 | V04 | V05 | V06 | V07 | V08 | V09 | V10 | V11 | V12 |
| | Trial timelines¤ | | | | | | | | | | | |
| | D0 | D2 | D4 | D6 | D8 | D10 | D12 | D14 | D16 | D28 | D180 | D365 |
| Time Windows | | | | | | ±1 d | ±1 d | | | ±4 d | ±15 d | ±30 d |
| Clinical Examination | ✓ | ✓ | ✓ | ✓ | ✓ | ✓ | ✓ | ✓ | ✓ | ✓ | ✓ | ✓ |
| Vital signs (BP, pulse rate) | ✓ | | | | | | | | | | | |
| Oral temperature | ✓ | ✓ | ✓ | ✓ | ✓ | ✓ | ✓ | ✓ | ✓ | ✓ | | |
| Blood Sampling: | | | | | | | | | | | | |
| Serology HBV/HCV/HIV | ✓ | | ✓ | | ✓ | | ✓ | | ✓ | ✓ | | |
| Biological Safety | ✓ | ✓ | ✓ | ✓ | ✓ | ✓ | ✓ | ✓ | ✓ | | | |
| Viremia | ✓ | | | | | | | | ✓ | ✓ | ✓ | ✓ |
| Immunogenicity | ✓ | ✓ | ✓ | ✓ | ✓ | ✓ | ✓ | ✓ | ✓ | ✓ | | |
| Cytokines in serum | ✓ | | | | | | | | | ✓ | | |

TABLE 12-continued

| Flow chart for follow up | | | | | | | | | | | | |
|---|---|---|---|---|---|---|---|---|---|---|---|---|
| | Visit Number | | | | | | | | | | | |
| | V01 | V02 | V03 | V04 | V05 | V06 | V07 | V08 | V09 | V10 | V11 | V12 |
| | Trial timelines¤ | | | | | | | | | | | |
| | D0 | D2 | D4 | D6 | D8 | D10 | D12 | D14 | D16 | D28 | D180 | D365 |
| PBMCs for T cell (subset) | ✓ | | | | | | | | | ✓ | | |
| immediate surveillance | ✓ | | | | | | | | | | | |
| Local & systemic events | ✓ | ✓ | ✓ | ✓ | ✓ | ✓ | ✓ | ✓ | ✓ | ✓ | ✓ | ✓ |

V: visit
D: day
¤Time intervals between visits will be calculated from the date of study vaccination which might differ from the date of visit (e.g. in case a temporary exclusion criterion is met). V06 and V07 must be done with at least 1-day interval.

The products tested are:

The vaccine evaluated is a lyophilised product in a vial that is reconstituted extemporaneously with the diluent provided separately:

Active ingredient: 4±0.5 $\log_{10}$ $CCID_{50}$ of either monovalent Vero dengue virus serotype 1 (VDV1) per 0.5 mL dose;

Diluent: Sterile NaCl 4% o solution for vaccine reconstitution.

The reconstituted vaccine, i.e 0.5 mL of NaCl 4% o solution of monovalent VDV1, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril® is presented as a lyophilised, avian-leukosis-free, stabilised product to be reconstituted with a diluent immediately before use. (Active ingredient: Live attenuated yellow fever virus (17D strain): ≧1,000 mouse Lethal Dose 50% ($LD_{50}$)/Diluent: Sterile NaCl 4% o solution).

The control vaccine is administered subcutaneously in the deltoid region.

The preliminary results of the trial are reported in Table 13 below.

TABLE 13

| preliminary safety data | | | | | | | | | | | | | | |
|---|---|---|---|---|---|---|---|---|---|---|---|---|---|---|
| | Day 0 | Day 1 | Day 2 | Day 3 | Day 4 | Day 5 | Day 6 | Day 7 | Day 8 | Day 9 | Day 10 | Day 11 | Day 12 | Day 13 |
| LOCAL SOLICITED | | | | | | | | | | | | | | |
| Pain | 1 | | | | | | | | | | | | | |
| Erythema | | | | | | | | | | | | | | |
| Induration | | | | | | | | | 1 | | | | | |
| Edema | | | | | | | | | | | | | | |
| LOCAL UNSOLICITED | | | | | | | | | | | | | | |
| Bruise | | 1 | 1 | | | | | | | | | | | |
| Pruritis | | | | | | | | | | | | | | |
| OTHER SOLICITED | | | | | | | | | | | | | | |
| Temp ≧37.5 C. | | | 1 | | | 1 | | | | | | | | |
| Rigors | | | 1 | 1 | | | | | 1 | | | | | |
| Malaise | | 2 | 1 | 1 | 1 | 1 | 1 | 1 | 1 | | | 2 | 1 | 2 |
| Asthenia | | 1 | 2 | 1 | 1 | 2 | 1 | | 1 | | | 2 | 1 | 1 |
| Anorexia | | | 1 | 1 | 1 | | | | | | | 1 | 1 | 1 |
| Nausea | | 1 | 2 | 1 | | 1 | 1 | | 1 | | | 1 | 1 | 2 |
| Vomiting | | | 1 | 1 | | 1 | 1 | | | | | 1 | 1 | |
| Stomach Pain | 1 | 1 | 2 | 2 | 1 | 1 | 1 | | 1 | | | 1 | 1 | 1 |
| Headache | 2 | 1 | 2 | 2 | | 1 | 1 | 1 | 2 | 1 | | 1 | 1 | 1 |
| Myalgia | | | 1 | 1 | | 1 | | | | | | 1 | 1 | 2 |
| Arthralgia | | | 1 | 1 | | 1 | 1 | | | | | 1 | 1 | 1 |
| Avoidance of light | | | | | | | 1 | 1 | | | | 1 | | |
| Conjunctivitis | | | | | | | | | | | | | | |
| Eye Pain | | | | | | | 1 | 1 | | | | | | |
| RASH | | | | | | | | | | | | | | |
| Macular | | | | | | | | | | 1 (1%) | | | | |
| Papular | | 1 (1%) | | | | | | | | | | | | |
| Maculo-papular | | | | | | | | | | | | | 1 (90%) | 1 (90%) |

TABLE 13-continued preliminary safety data

| | Day 0 | Day 1 | Day 2 | Day 3 | Day 4 | Day 5 | Day 6 | Day 7 | Day 8 | Day 9 | Day 10 | Day 11 | Day 12 | Day 13 |
|---|---|---|---|---|---|---|---|---|---|---|---|---|---|---|
| OTHER UNSOLICITED | | | | | | | | | | | | | | |
| Decreased WCC | | | | | | | | | 2 | | 1 | | | |
| Neutropenia | | | | | | | | | 2 | | 1 | | | |
| Increased aPPT | | | | | 1 | | | | 1 | | | | | |
| Elevated CK | | | | | | | | | 1 | | | | | |
| Odd dreams | | | | | | | 1 | | | | | | | |
| Low abdo pain (kidneys/liver) | | | | | | | | | | | | 1 | 1 | 1 |
| Diarrhoea | | 1 | 1 | 1 | 1 | 1 | | | | | 1 | 1 | 1 | 1 |
| Sore throat | | | | 1 | | | | | | | | | | 1 |
| Cough | | | | | | | | | | | | | | 1 |
| Early menstruation | | | | | | | | | 1 | | | | | |
| Tiredness | | | | | | | | | | | 1 | | | |

Table 13 shows that biological abnormalities (WCC reductions, platelet count reductions) have all been mild. The symptoms have been mainly malaise, nausea, diarrhoea and occasional vomiting. They have been of moderate severity. One significant rash—typical "viral" maculopapular rash, onset day 12, 90% coverage.

The safety data of the second cohort are also satisfactory with no biological abnormality recorded. All subjects have antibody response 28 days after vaccination against dengue 1 (titer between 1315 and 13150).

REFERENCES

Bhamarapravati, N and Yoksan S. (1997). Dengue and Dengue Hemorrhagic Fever. Live attenuated tetravalent dengue vaccines, CABI Publishing, 367-379.

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press:223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Huang et al. (2000). J. Virol 74; 3020-3028.

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Rigau-Perez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travellers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9.

WHO Technical Guide, 1986. Dengue haemorrhagic fever: diagnosis, treatment and control, p 1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

What is claimed is:

1. An isolated nucleic acid which comprises the DNA sequence SEQ ID NO: 1 or its equivalent RNA sequence.

2. The isolated nucleic acid according to claim 1 wherein the deoxythymidines are replaced by uridines.

3. The isolated nucleic acid according to claim 1 wherein the sequence encodes the dengue serotype I virus (VDV1) strain.

4. An isolated nucleic acid encoding the polyprotein having the sequence SEQ ID NO:41.

* * * * *

SEQUENCE LISTING

```
<160> NUMBER OF SEQ ID NOS: 44

<210> SEQ ID NO 1
<211> LENGTH: 10735
<212> TYPE: DNA
<213> ORGANISM: Dengue virus
```

<220> FEATURE:
<221> NAME/KEY: misc_feature
<222> LOCATION: (1)..(10654)
<223> OTHER INFORMATION: VDV1

<400> SEQUENCE: 1

```
agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgagggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
```

-continued

```
cacgtctatg ggaaaactgg tacaccaggt ttttggaact gcatatggag ttttgtttag   2280
cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagacgttag   2700
tggaatcttg gcccaaggaa aaaaaatgat taggccacaa cccatggaac acaaatactc   2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctacccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
```

-continued

```
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
```

-continued cctgacagcc atcgcaaacc aagcagctat attgatggga cttgacaagg gatggccaat 7080
atcgaagatg gacataggag ttccacttct cgccttgggg tgctattccc aagtgaatcc 7140
gctgacactg atagcggcag tattgatgct agtagctcat tacgccataa ttggacctgg 7200
actgcaagca aaagctacta gagaagctca aaaaagaaca gcggctggaa taatgaaaaa 7260
tccaactgtc gacgggattg ttgcaataga cttagatccc gtggtttacg atgcaaaatt 7320
tgaaaaacag ctaggccaaa taatgttgtt gatactttgc acatcacaga ttcttttgat 7380
gcggactaca tgggccttgt gtgaatccat cacattggct actggacctc tgaccactct 7440
ttgggaggga tctccaggaa aattctggaa caccacaata gcggtatcca tggcaaacat 7500
tttcaggggg agttatctag caggagcagg tctggccttc tcattaatga aatctctagg 7560
aggaggtagg agaggcacgg gagcccaagg ggaaacactg ggagaaaaat ggaaaagaca 7620
actaaaccaa ctgagcaagt cagaattcaa tacttacaag aggagtggga ttatggaggt 7680
ggatagatcc gaagccaaag agggactgaa aagaggagaa acaaccaaac acgcagtatc 7740
gagaggaacg gccaaactga ggtggttcgt ggagaggaac cttgtgaaac cagaagggaa 7800
agtcatagac ctcggttgtg gaagaggtgg ctggtcatat tattgcgctg ggctgaagaa 7860
agtcacagaa gtgaaaggat acacaaaagg aggacctgga catgaggaac caatcccaat 7920
ggcgacctat ggatggaacc tagtaaggct gcactccgga aaagatgtat tttttatacc 7980
acctgagaaa tgtgacaccc ttttgtgtga tattggtgag tcctctccga acccaactat 8040
agaggaagga agaacgttac gtgttctgaa aatggtggaa ccatggctca gaggaaacca 8100
attttgcata aaaattctaa atccctatat gccgagcgtg gtagaaactc tggaacaaat 8160
gcaaagaaaa catggaggaa tgctagtgcg aaacccactc tcaagaaatt ccacccatga 8220
aatgtactgg gtttcatgtg gaacaggaaa cattgtgtca gcagtaaaca tgacatctag 8280
aatgttgcta aatcggttca caatggctca caggaagcca acatatgaaa gagacgtgga 8340
cttaggcgct ggaacaagac atgtggcagt agaaccagag gtagccaacc tagatatcat 8400
tggccagagg atagagaata taaaaaatga acataagtca acatggcatt atgatgagga 8460
caatccatac aaaacatggg cctatcatgg atcatatgag gttaagccat caggatcggc 8520
ctcatccatg gtcaatggcg tggtgagatt gctcaccaaa ccatgggatg ttatccccat 8580
ggtcacacaa atagccatga ctgataccac accctttgga caacagaggg tgtttaaaga 8640
gaaagttgac acgcgcacac caaaagcaaa acgtggcaca gcacaaatta tggaagtgac 8700
agccaggtgg ttatggggtt tcctttctag aaacaaaaaa cccagaattt gcacaagaga 8760
ggagtttaca agaaaagtta ggtcaaacgc agctattgga gcagtgttcg ttgatgaaaa 8820
tcaatggaac tcggcaaaag aagcagtgga agacgaacgg ttctgggaac ttgtccacag 8880
agagagggag cttcataaac aggggaaatg tgccacgtgt gtctacaata tgatggggaa 8940
gagagagaaa aaattaggag agttcggaaa ggcaaaagga agtcgtgcaa tatggtacat 9000
gtggttggga gcacgcttcc tagagtttga agcccttggt ttcatgaatg aagatcactg 9060
gttcagtaga gagaattcac tcagtggagt ggaaggagaa ggactccaca aacttggata 9120
catactcaga gacatatcaa ggattccagg ggggaacatg tatgcagatg acacagccgg 9180
atgggacaca agaataacag aggatgatct ccagaatgag gctaaaatca ctgacatcat 9240
ggagcccgaa catgccctgc tggctacgtc aatctttaag ctgacctacc aaaataaggt 9300
ggtaagggtg cagagaccag caaaaaatgg aaccgtgatg gatgttatat ccagacgtga 9360
ccagagaggc agtggacagg ttggaactta tggcttaaac actttcacca acatggaggc 9420

-continued ccaactgata agacaaatgg agtctgaggg aatcttttta cccagcgaat tggaaacccc 9480
aaatctagcc ggaagagttc tcgactggtt ggaaaaatat ggtgtcgaaa ggctgaaaag 9540
aatggcaatc agcggagatg actgtgtggt gaaaccaatt gatgacaggt tcgcaacagc 9600
cttaacagct ttgaatgaca tgggaaaagt aagaaaagac ataccacaat gggaaccttc 9660
aaaaggatgg aatgattggc aacaagtgcc tttctgttca caccacttcc accagctaat 9720
tatgaaggat gggagggaga tagtggtgcc atgccgcaac caagatgaac ttgtggggag 9780
ggccagagta tcacaaggcg ccggatggag cctgagagaa accgcatgcc taggcaagtc 9840
atatgcacaa atgtggcagc tgatgtattt ccacaggaga gacctgagac tggcggctaa 9900
cgctatttgt tcagccgttc cagttgattg ggtcccaacc agccgcacca cctggtcgat 9960
ccatgcccat caccaatgga tgacaacaga agacatgtta tcagtatgga atagggtctg 10020
gatagaggaa aacccatgga tggaggataa gactcatgtg tccagttggg aagaagttcc 10080
atacctagga aagagggaag atcagtggtg tggatccctg ataggcttaa cagcaagggc 10140
cacctgggcc actaatatac aagtggccat aaaccaagtg agaaggctca ttgggaatga 10200
gaattatcta gattacatga catcaatgaa gagattcaag aatgagagtg atcccgaagg 10260
ggcactctgg taagtcaaca cattcacaaa ataaaggaaa ataaaaaatc aaatgaggca 10320
agaagtcagg ccagattaag ccatagtacg gtaagagcta tgctgcctgt gagccccgtc 10380
caaggacgta aaatgaagtc aggccgaaag ccacggtttg agcaagccgt gctgcctgtg 10440
gctccatcgt ggggatgtaa aaacccggga ggctgcaacc catggaagct gtacgcatgg 10500
ggtagcagac tagtggttag aggagacccc tcccaagaca caacgcagca gcggggccca 10560
acaccagggg aagctgtacc ctggtggtaa ggactagagg ttagaggaga ccccccgcgt 10620
aacaataaac agcatattga cgctgggaga gaccagagat cctgctgtct ctacagcatc 10680
attccaggca cagaacgcca gaaaatggaa tggtgctgtt gaatcaacag gttct 10735

<210> SEQ ID NO 2
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: Dengue virus type 1 strain 16007 polyprotein precursor, complete cds

<400> SEQUENCE: 2
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgagggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgcccccg 600
gatcactgag gcggaaccag atgacgttga ctgttggtgc aatgccacgg acacatgggt 660
gacctatgga acgtgctctc aaactggcga acaccgacga gacaaacgtt ccgtcgcatt 720

-continued

```
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agttcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa gaaagatcat ggcttgtcca   1560
caaacaatgg tttctagact taccactgcc ttggacctct ggggcttcaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt tttggaact gcatatggag ttttgtttag   2280
cggagtttct tggaccatga aaataggaat agggattctg ctgacatggc taggattaaa   2340
ttcaaggaac acgtcccttt cgatgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagatgttag   2700
tggaatcttg gcccaaggga aaaaaatgat taggccacaa cccatggaac acaaatactc   2760
gtggaaaagc tggggaaaag ccaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
```

-continued

```
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctaccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acgaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
```

-continued

```
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctatg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcatgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacaa ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
```

-continued

```
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtccgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
```

-continued

```
agaagtcagg ccagattaag ccatagtacg gtaagagcta tgctgcctgt gagccccgtc  10380

caaggacgta aaatgaagtc aggccgaaag ccacggtttg agcaagccgt gctgcctgtg  10440

gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga cccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735


<210> SEQ ID NO 3
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV-1
      Dengue virus type 1 strain 16007 (PDK-13) polyprotein precursor,
      complete cds

<400> SEQUENCE: 3

agttgttagt ctacgtggac cgacaagaac agtttcgaat cggaagcttg cttaacgtag     60

ttctaacagt tttttattag agagcagatc tctgatgatc aaccaacgaa aaaagacggg    120

tcgaccgtct ttcaatatgc tgaaacgcgc gagaaaccgc gtgtcaactg tttcacagtt    180

ggcgaagaga ttctcaaaag gattgctctc aggccaagga cccatgaaat tggtgatggc    240

tttcatagca ttcttaagat ttctagccat acccccaaca gcaggaattt tggctagatg    300

gggctcattc aagaagaatg gagcgattaa agtgttacgg ggtttcaaga gagaaatctc    360

aaacatgcta aacataatga acaggaggaa aagatccgtg accatgctcc ttatgctgct    420

gcccacagcc ctggcgttcc atctgacgac acgaggggga gagccgcata tgatagttag    480

caagcaggaa agaggaaagt cacttttgtt caagacctct gcaggtgtca acatgtgcac    540

cctcattgcg atggatttgg gagagttgtg tgaggacacg atgacctaca aatgcccccg    600

gatcactgag gcggaaccag atgacgttga ctgttggtgc aatgccacgg acacatgggt    660

gacctatgga acgtgctctc aaactggcga acaccgacga gacaaacgtt ccgtcgcatt    720

ggccccacac gtggggcttg gcctagaaac aagagccgaa acgtggatgt cctctgaagg    780

tgcttggaaa cagatacaaa aagtagagac ttgggctctg agacatccag gattcacggt    840

gatagccctt tttctagcac atgccatagg aacatccatc acccagaaag ggatcatttt    900

cattttgctg atgctggtaa caccatctat ggccatgcga tgcgtgggaa taggcaacag    960

agacttcgtg gaaggactgt caggagcaac atgggtggat gtggtactgg agcatggaag   1020

ttgcgtcacc accatggcaa aaaacaaacc aacactggac attgaactct tgaagacgga   1080

ggtcacaaac cctgcagttc tgcgtaaatt gtgcattgaa gctaaaatat caaacaccac   1140

caccgattcg agatgtccaa cacaaggaga agccacactg gtggaagaac aagacgcgaa   1200

ctttgtgtgc cgacgaacgt tcgtggacag aggctggggc aatggctgtg ggctattcgg   1260

aaaaggtagt ctaataacgt gtgccaagtt taagtgtgtg acaaaactag aaggaaagat   1320

agctcaatat gaaaacctaa aatattcagt gatagtcacc gtccacactg gagatcagca   1380

ccaggtggga aatgagacta cagaacatgg aacaactgca accataacac ctcaagctcc   1440

tacgtcggaa atacagctga ccgactacgg aaccettaca ttagattgtt cacctaggac   1500

agggctagat tttaacgaga tggtgttgct gacaatgaaa aagaaatcat ggcttgtcca   1560
```

-continued caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860
gaaagaagtg gctgagaccc agcatggaac tgttctggtg caggttaaat atgaaggaac 1920
agacgcacca tgcaagattc ccttttcgac ccaagatgag aaaggagcaa cccagaatgg 1980
gagattaata acagccaacc ccatagtcac tgacaaagaa aaaccagtca atattgaggc 2040
agaaccaccc tttggtgaga gctacatcgt ggtaggagca ggtgaaaaag ctttgaaact 2100
aagctggttc aagaaaggaa gcagcatagg gaaaatgttt gaagcaactg cccgaggagc 2160
acgaaggatg gccattctgg gagacaccgc atgggacttc ggttctatag gaggagtgtt 2220
cacgtctatg ggaaaactgg tacaccaggt tttggaact gcatatggag ttttgtttag 2280
cggagtttct tggaccatga aaataggaat agggattctg ctgacatggc taggattaaa 2340
ttcaaggaac acgtcccttt cggtgatgtg catcgcagtt ggcatggtca cactgtacct 2400
aggagtcatg gttcaggcag attcgggatg tgtaatcaac tggaaaggca gagaacttaa 2460
atgtggaagc ggcatttttg tcactaatga agttcacact tggacagagc aatacaaatt 2520
ccaggctgac tcccccaaga gactatcagc agccattggg aaggcatggg aggagggtgt 2580
gtgtggaatc cgatcagcca ctcgtctcga gaacatcatg tggaaacaaa tatcaaatga 2640
attgaaccac atcctacttg aaaatgacat gaaatttaca gtggtcgtgg gagacgttag 2700
tggaatcttg gcccaaggga aaaaaatgat taggccacaa cccatggaac acaaatactc 2760
gtggaaaagc tggggaaaag ctaaaatcat aggagcggat gtacagaaca ccaccttcat 2820
catcgacggc ccaaacaccc cagaatgccc tgacaatcaa agagcatgga atatttggga 2880
agtagaggac tatggatttg ggattttcac gacaaacata tggttgaaat tgcgtgactc 2940
ctacacccaa gtatgtgacc accggctgat gtcagctgcc attaaggaca gcaaggcagt 3000
ccatgctgac atggggtact ggatagaaag tgaaaagaac gagacatgga agttggcgag 3060
agcctccttt atagaagtta agacatgcat ctggccaaaa tcccacactc tatggagcaa 3120
tggagttctg gaaagtgaaa tgataattcc aaagatatat ggaggaccaa tatctcagca 3180
caactacaga ccaggatatt tcacacaaac agcagggccg tggcacctag gcaagttgga 3240
actagatttc gatttttgtg aaggtaccac agttgttgtg gatgaacatt gtggaaatcg 3300
aggaccatct ctcagaacca caacagtcac aggaaagata atccatgaat ggtgctgcag 3360
atcttgtacg ctaccccccc tacgtttcaa aggggaagac gggtgttggt acggcatgga 3420
aatcagacca gtgaaggaca aggaagagaa cctggtcaag tcaatggtct ctgcagggtc 3480
aggagaagtg gacagctttt cactaggact gctatgcata tcaataatga ttgaagaagt 3540
gatgagatcc agatggagca aaaaaatgct gatgactgga acactggctg tgttcctcct 3600
tcttataatg ggacaattga catggagtga tctgatcagg ttatgtatta tggttggagc 3660
caacgcttca gacaagatgg ggatgggaac aacgtaccta gctttaatgg ccactttcaa 3720
aatgagacca atgttcgccg tcgggctatt atttcgcaga ctaacatcta gagaagttct 3780
tcttcttaca attggcttga gcctggtggc atccgtggag ctaccaagtt ccctagagga 3840
gctgggggat ggacttgcaa taggcatcat gatgttgaaa ttattgactg attttcagtc 3900
acaccagcta tgggctactc tgctatcctt gacatttatt aaaacaactt tttcattgca 3960

-continued

```
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
```

-continued

```
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
```

-continued

```
ggagtttaca agaaaagtta ggtcaaacgc agctattgga gcagtgttcg ttgatgaaaa   8820

tcaatggaac tcggcaaaag aagcagtgga agacgaacgg ttctgggaac ttgtccacag   8880

agagagggag cttcataaac aggggaaatg tgccacgtgt gtctacaata tgatggggaa   8940

gagagagaaa aaattaggag agttcggaaa ggcaaaagga agtcgtgcaa tatggtacat   9000

gtggttggga gcacgcttcc tagagtttga agcccttggt ttcatgaatg aagatcactg   9060

gttcagtaga gagaattcac tcagtggagt ggaaggagaa ggactccaca aacttggata   9120

catactcaga gacatatcaa ggattccagg ggggaacatg tatgcagatg acacagccgg   9180

atgggacaca agaataacag aggatgatct ccagaatgag gctaaaatca ctgacatcat   9240

ggagcccgaa catgccctgc tggctacgtc aatctttaag ctgacctacc aaaataaggt   9300

ggtaagggtg cagagaccag caaaaaatgg aaccgtgatg gatgttatat ccagacgtga   9360

ccagagaggc agtggacagg ttggaactta tggcttaaac actttcacca acatggaggc   9420

ccaactgata agacaaatgg agtctgaggg aatcttttta cccagcgaat tggaaacccc   9480

aaatctagcc ggaagagttc tcgactggtt ggaaaaatat ggtgtcgaaa ggctgaaaag   9540

aatggcaatc agcggagatg actgtgtggt gaaaccaatt gatgacaggt tcgcaacagc   9600

cttaacagct ttgaatgaca tgggaaaagt aagaaaagac ataccacaat gggaaccttc   9660

aaaaggatgg aatgattggc aacaagtgcc tttctgttca caccacttcc accagctaat   9720

tatgaaggat gggagggaga tagtggtgcc atgccgcaac caagatgaac ttgtggggag   9780

ggccagagta tcacaaggcg ccggatggag cctgagagaa accgcatgcc taggcaagtc   9840

atatgcacaa atgtggcagc tgatgtattt ccacaggaga gacctgagac tggcggctaa   9900

cgctatttgt tcagccgttc cagttgattg ggtcccaacc agccgcacca cctggtcgat   9960

ccatgcccat caccaatgga tgacaacaga agacatgtta tcagtatgga atagggtctg  10020

gatagaggaa aacccatgga tggaggataa gactcatgtg tccagttggg aagaagttcc  10080

atacctagga aagagggaag atcagtggtg tggatccctg ataggcttaa cagcaagggc  10140

cacctgggcc actaatatac aagtggccat aaaccaagtg agaaggctca ttgggaatga  10200

gaattatcta gattacatga catcaatgaa gagattcaag aatgagagtg atcccgaagg  10260

ggcactctgg taagtcaaca cattcacaaa ataaaggaaa ataaaaaatc aaatgaggca  10320

agaagtcagg ccagattaag ccatagtacg gtaagagcta tgctgcctgt gagccccgtc  10380

caaggacgta aaatgaagtc aggccgaaag ccacggtttg agcaagccgt gctgcctgtg  10440

gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735
```

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4

```
gttttcccag tcacgactac gtggaccgac aagaacag                           38
```

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
aacagctatg accatgggat ggagttacca gcatcag 37

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
gttttcccag tcacgactga acaccgacga gacaaac 37

<210> SEQ ID NO 7
<211> LENGTH: 36
<212> TYPE: DNA
<213> ORGANISM: Artificial sequence
<220> FEATURE:
<223> OTHER INFORMATION: primer

<400> SEQUENCE: 7
aacagctatg accatgaggt ccaaggcagt ggtaag 36

<210> SEQ ID NO 8
<211> LENGTH: 38
<212> TYPE: DNA
<213> ORGANISM: Artificial sequence
<220> FEATURE:
<223> OTHER INFORMATION: primer

<400> SEQUENCE: 8
gttttcccag tcacgacttg gaaatgagac cacagaac 38

<210> SEQ ID NO 9
<211> LENGTH: 36
<212> TYPE: DNA
<213> ORGANISM: Artificial sequence
<220> FEATURE:
<223> OTHER INFORMATION: primer

<400> SEQUENCE: 9
aacagctatg accatggaaa caccgctgaa caaaac 36

<210> SEQ ID NO 10
<211> LENGTH: 36
<212> TYPE: DNA
<213> ORGANISM: Artificial sequence
<220> FEATURE:
<223> OTHER INFORMATION: primer

<400> SEQUENCE: 10
gttttcccag tcacgacggt tcaagaaggg aagcag 36

<210> SEQ ID NO 11
<211> LENGTH: 37
<212> TYPE: DNA
<213> ORGANISM: Artificial sequence
<220> FEATURE:
<223> OTHER INFORMATION: primer -continued

<400> SEQUENCE: 11
aacagctatg accatgttct atccagtacc ccatgtc 37

<210> SEQ ID NO 12
<211> LENGTH: 39
<212> TYPE: DNA
<213> ORGANISM: Artificial sequence
<220> FEATURE:
<223> OTHER INFORMATION: primer

<400> SEQUENCE: 12
gttttcccag tcacgaccag aataccacct tcatcatcg 39

<210> SEQ ID NO 13
<211> LENGTH: 35
<212> TYPE: DNA
<213> ORGANISM: Artificial sequence
<220> FEATURE:
<223> OTHER INFORMATION: primer

<400> SEQUENCE: 13
aacagctatg accatgttcc catccccatc ttgtc 35

<210> SEQ ID NO 14
<211> LENGTH: 39
<212> TYPE: DNA
<213> ORGANISM: Artificial sequence
<220> FEATURE:
<223> OTHER INFORMATION: primer

<400> SEQUENCE: 14
gttttcccag tcacgacgga aatcagacca gtcaaggag 39

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
aacagctatg accatgtgtt gtgtgaggca ccagag 36

<210> SEQ ID NO 16
<211> LENGTH: 38
<212> TYPE: DNA
<213> ORGANISM: Artificial sequence
<220> FEATURE:
<223> OTHER INFORMATION: primer

<400> SEQUENCE: 16
gttttcccag tcacgacgca aaccactaac catgtttc 38

<210> SEQ ID NO 17
<211> LENGTH: 35
<212> TYPE: DNA
<213> ORGANISM: Artificial sequence
<220> FEATURE:
<223> OTHER INFORMATION: primer

<400> SEQUENCE: 17
aacagctatg accatgccac ttgttgtcac cactc 35

-continued

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
gttttcccag tcacgaccca agggaagaga ctggaac 37

<210> SEQ ID NO 19
<211> LENGTH: 37
<212> TYPE: DNA
<213> ORGANISM: Artificial sequence
<220> FEATURE:
<223> OTHER INFORMATION: primer

<400> SEQUENCE: 19
aacagctatg accatgtcct gatttgatgc ttggaac 37

<210> SEQ ID NO 20
<211> LENGTH: 38
<212> TYPE: DNA
<213> ORGANISM: Artificial sequence
<220> FEATURE:
<223> OTHER INFORMATION: primer

<400> SEQUENCE: 20
gttttcccag tcacgacaag cacattttac cgatccag 38

<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
aacagctatg accatggtcg tagtttcttt ctttctcctt c 41

<210> SEQ ID NO 22
<211> LENGTH: 37
<212> TYPE: DNA
<213> ORGANISM: Artificial sequence
<220> FEATURE:
<223> OTHER INFORMATION: primer

<400> SEQUENCE: 22
gttttcccag tcacgacgca atagacgggg aatacag 37

<210> SEQ ID NO 23
<211> LENGTH: 36
<212> TYPE: DNA
<213> ORGANISM: Artificial sequence
<220> FEATURE:
<223> OTHER INFORMATION: primer

<400> SEQUENCE: 23
aacagctatg accatgatga tggtggtttt cagcag 36

<210> SEQ ID NO 24
<211> LENGTH: 37
<212> TYPE: DNA
<213> ORGANISM: Artificial sequence
<220> FEATURE:
<223> OTHER INFORMATION: primer -continued

<400> SEQUENCE: 24
gttttcccag tcacgacgtg ttgcttattc cagagcc 37

<210> SEQ ID NO 25
<211> LENGTH: 38
<212> TYPE: DNA
<213> ORGANISM: Artificial sequence
<220> FEATURE:
<223> OTHER INFORMATION: primer

<400> SEQUENCE: 25
aacagctatg accatggctg tcttttccat ttttctcc 38

<210> SEQ ID NO 26
<211> LENGTH: 37
<212> TYPE: DNA
<213> ORGANISM: Artificial sequence
<220> FEATURE:
<223> OTHER INFORMATION: primer

<400> SEQUENCE: 26
gttttcccag tcacgacact ttgcacatca cagatcc 37

<210> SEQ ID NO 27
<211> LENGTH: 35
<212> TYPE: DNA
<213> ORGANISM: Artificial sequence
<220> FEATURE:
<223> OTHER INFORMATION: primer

<400> SEQUENCE: 27
aacagctatg accatgttcg cactagcatt cctcc 35

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
gttttcccag tcacgaccac ctgagaaatg tgacacc 37

<210> SEQ ID NO 29
<211> LENGTH: 38
<212> TYPE: DNA
<213> ORGANISM: Artificial sequence
<220> FEATURE:
<223> OTHER INFORMATION: primer

<400> SEQUENCE: 29
aacagctatg accatgtttc cttgtttatg aagctccc 38

<210> SEQ ID NO 30
<211> LENGTH: 36
<212> TYPE: DNA
<213> ORGANISM: Artificial sequence
<220> FEATURE:
<223> OTHER INFORMATION: primer

<400> SEQUENCE: 30
gttttcccag tcacgaccaa aagcgaaacg aggcac 36

-continued

<210> SEQ ID NO 31
<211> LENGTH: 38
<212> TYPE: DNA
<213> ORGANISM: Artificial sequence
<220> FEATURE:
<223> OTHER INFORMATION: primer

<400> SEQUENCE: 31
aacagctatg accatggttt caccacacag tcatctcc 38

<210> SEQ ID NO 32
<211> LENGTH: 37
<212> TYPE: DNA
<213> ORGANISM: Artificial sequence
<220> FEATURE:
<223> OTHER INFORMATION: primer

<400> SEQUENCE: 32
gttttcccag tcacgacaga ccagcgaaaa atggaac 37

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgtccc aatgagcctt ctcac 35

<210> SEQ ID NO 34
<211> LENGTH: 38
<212> TYPE: DNA
<213> ORGANISM: Artificial sequence
<220> FEATURE:
<223> OTHER INFORMATION: primer

<400> SEQUENCE: 34
gttttcccag tcacgacgct aatgctatct gttcagcc 38

<210> SEQ ID NO 35
<211> LENGTH: 36
<212> TYPE: DNA
<213> ORGANISM: Artificial sequence
<220> FEATURE:
<223> OTHER INFORMATION: primer

<400> SEQUENCE: 35
aacagctatg accatgtgat tcaacagcac cattcc 36

<210> SEQ ID NO 36
<211> LENGTH: 17
<212> TYPE: DNA
<213> ORGANISM: Artificial sequence
<220> FEATURE:
<223> OTHER INFORMATION: primer

<400> SEQUENCE: 36
ccatggaagc tgtacgc 17

<210> SEQ ID NO 37
<211> LENGTH: 19
<212> TYPE: DNA
<213> ORGANISM: Artificial sequence
<220> FEATURE:
<223> OTHER INFORMATION: primer

<400> SEQUENCE: 37
gagacagcag gatctctgg 19

<210> SEQ ID NO 38
<211> LENGTH: 17
<212> TYPE: DNA
<213> ORGANISM: Artificial sequence
<220> FEATURE:
<223> OTHER INFORMATION: primer tail

<400> SEQUENCE: 38
gttttcccag tcacgac 17

<210> SEQ ID NO 39
<211> LENGTH: 16
<212> TYPE: DNA
<213> ORGANISM: Artificial sequence
<220> FEATURE:
<223> OTHER INFORMATION: primer tail

<400> SEQUENCE: 39
aacagctatg accatg 16

<210> SEQ ID NO 40
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: VDV2
<220> FEATURE:
<221> NAME/KEY: misc_feature
<222> LOCATION: (10361)..(10361)
<223> OTHER INFORMATION: n=A or T or G or C

<400> SEQUENCE: 40
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgcgaat gggactggag acacgaactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080

-continued

```
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaagag   1620
tcaaattgga tacagaagga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaaa   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
```

-continued catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac caacatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tcacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctga gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880

```
gcagcacaaa gaagagggag aataggaaga aatccaaaaa atgagaatga ccagtacata    5940

tacatggggg aacctctgga aaatgatgaa gactgtgcac actggaaaga agctaaaatg    6000

ctcctagata acatcaacac gccagaagga atcattccta gcatgttcga accagagcgt    6060

gaaaaggtgg atgccattga tggcgaatac cgcttgagag gagaagcaag gaaaaccttt    6120

gtagacttaa tgagaagagg agacctacca gtctggttgg cctacagagt ggcagctgaa    6180

ggcatcaact acgcagacag aaggtggtgt tttgatggag tcaagaacaa ccaaatccta    6240

gaagaaaacg tggaagttga aatctggaca aaagaagggg aaaggaagaa attgaaaccc    6300

agatggttgg atgctaggat ctattctgac ccactggcgc taaaagaatt taaggaattt    6360

gcagccggaa gaaagtctct gaccctgaac ctaatcacag aaatgggtag gctcccaacc    6420

ttcatgactc agaaggcaag agacgcactg gacaacttag cagtgctgca cacggctgag    6480

gcaggtggaa gggcgtacaa ccatgctctc agtgaactgc cggagaccct ggagacattg    6540

cttttactga cacttctggc tacagtcacg ggagggatct ttttattctt gatgagcgca    6600

aggggcatag ggaagatgac cctgggaatg tgctgcataa tcacggctag catcctccta    6660

tggtacgcac aaatacagcc acactggata gcagcttcaa taatactgga gttttttctc    6720

atagttttgc ttattccaga acctgaaaaa cagagaacac cccaagacaa ccaactgacc    6780

tacgttgtca tagccatcct cacagtggtg gccgcaacca tggcaaacga gatgggtttc    6840

ctagaaaaaa cgaagaaaga tctcggattg ggaagcattg caacccagca acccgagagc    6900

aacatcctgg acatagatct acgtcctgca tcagcatgga cgctgtatgc cgtggccaca    6960

acatttgtta caccaatgtt gagacatagc attgaaaatt cctcagtgaa tgtgtcccta    7020

acagctatag ccaaccaagc cacagtgtta atgggtctcg ggaaaggatg gccattgtca    7080

aagatggaca tcggagttcc ccttctcgcc attggatgct actcacaagt caaccccata    7140

actctcacag cagctctttt cttattggta gcacattatg ccatcatagg gccaggactc    7200

caagcaaaag caaccagaga agctcagaaa agagcagcgg cgggcatcat gaaaaaccca    7260

actgtcgatg gaataacagt gattgaccta gatccaatac cttatgatcc aaagtttgaa    7320

aagcagttgg gacaagtaat gctcctagtc ctctgcgtga ctcaagtatt gatgatgagg    7380

actacatggg ctctgtgtga ggctttaacc ttagctaccg ggcccatctc cacattgtgg    7440

gaaggaaatc cagggaggtt ttggaacact accattgcgg tgtcaatggc taacattttt    7500

agagggagtt acttggccgg agctggactt ctcttttcta ttatgaagaa cacaaccaac    7560

acaagaaggg gaactggcaa cataggagag acgcttggag agaaatggaa aagccgattg    7620

aacgcattgg gaaaaagtga attccagatc tacaagaaaa gtggaatcca ggaagtggat    7680

agaaccttag caaagaaggg cattaaaaga ggagaaacgg accatcacgc tgtgtcgcga    7740

ggctcagcaa aactgagatg gttcgttgag agaaacatgg tcacaccaga agggaaagta    7800

gtggacctcg gttgtggcag aggaggctgg tcatactatt gtggaggact aaagaatgta    7860

agagaagtca aaggcctaac aaaaggagga ccaggacacg aagaacccat ccccatgtca    7920

acatatgggt ggaatctagt gcgtcttcaa agtggagttg acgttttctt catcccgcca    7980

gaaaagtgtg acacattatt gtgtgacata ggggagtcat caccaaatcc cacagtggaa    8040

gcaggacgaa cactcagagt ccttaactta gtagaaaatt ggttgaacaa caacactcaa    8100

ttttgcataa aggttctcaa cccatatatg ccctcagtca tagaaaaaat ggaagcacta    8160

caaaggaaat atggaggagc cttagtgagg aatccactct cacgaaactc cacacatgag    8220

atgtactggg tatccaatgc ttccgggaac atagtgtcat cagtgaacat gatttcaagg    8280
```

-continued

```
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa aaatcacact agaagaccta aaaaatgaag agatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aaacatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc naggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagggga gacccctccc ttacaaatcg cagcaacaat gggggcccaa ggcgagatga  10560
agctgtagtc tcgctggaag gactagaggt tagaggagac ccccccgaaa caaaaaacag  10620
```

-continued catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 41
<211> LENGTH: 3392
<212> TYPE: PRT
<213> ORGANISM: Dengue virus
<220> FEATURE:
<221> NAME/KEY: CHAIN
<222> LOCATION: (1)..(114)
<223> OTHER INFORMATION: capsid protein
<220> FEATURE:
<221> NAME/KEY: CHAIN
<222> LOCATION: (115)..(280)
<223> OTHER INFORMATION: premembrane protein
<220> FEATURE:
<221> NAME/KEY: CHAIN
<222> LOCATION: (281)..(775)
<223> OTHER INFORMATION: envelope glycoprotein
<220> FEATURE:
<221> NAME/KEY: CHAIN
<222> LOCATION: (776)..(1127)
<223> OTHER INFORMATION: nonstructural protein 1
<220> FEATURE:
<221> NAME/KEY: CHAIN
<222> LOCATION: (1128)..(1345)
<223> OTHER INFORMATION: nonstructural protein 2A
<220> FEATURE:
<221> NAME/KEY: CHAIN
<222> LOCATION: (1346)..(1475)
<223> OTHER INFORMATION: nonstructural protein 2B
<220> FEATURE:
<221> NAME/KEY: CHAIN
<222> LOCATION: (1476)..(2094)
<223> OTHER INFORMATION: nonstructural protein 3
<220> FEATURE:
<221> NAME/KEY: CHAIN
<222> LOCATION: (2095)..(2244)
<223> OTHER INFORMATION: nonstructural protein 4A
<220> FEATURE:
<221> NAME/KEY: CHAIN
<222> LOCATION: (2245)..(2493)
<223> OTHER INFORMATION: nonstructural protein 4B
<220> FEATURE:
<221> NAME/KEY: CHAIN
<222> LOCATION: (2494)..(3392)
<223> OTHER INFORMATION: nonstructural protein 5

<400> SEQUENCE: 41

Met Ile Asn Gln Arg Lys Lys Thr Gly Arg Pro Ser Phe Asn Met Leu
1 5 10 15

Lys Arg Ala Arg Asn Arg Val Ser Thr Val Ser Gln Leu Ala Lys Arg
20 25 30

Phe Ser Lys Gly Leu Leu Ser Gly Gln Gly Pro Met Lys Leu Val Met
35 40 45

Ala Phe Ile Ala Phe Leu Arg Phe Leu Ala Ile Pro Pro Thr Ala Gly
50 55 60

Ile Leu Ala Arg Trp Gly Ser Phe Lys Lys Asn Gly Ala Ile Lys Val
65 70 75 80

Leu Arg Gly Phe Lys Arg Glu Ile Ser Asn Met Leu Asn Ile Met Asn
85 90 95

Arg Arg Lys Arg Ser Val Thr Met Leu Leu Met Leu Leu Pro Thr Ala
100 105 110

Leu Ala Phe His Leu Thr Thr Arg Gly Gly Glu Pro His Met Ile Val
115 120 125

Ser Lys Gln Glu Arg Gly Lys Ser Leu Leu Phe Lys Thr Ser Ala Gly
130 135 140

```
Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Ala Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Lys Lys Ser Trp Leu Val His Lys Gln Trp Phe Leu Asp Leu
                485                 490                 495

Pro Leu Pro Trp Thr Ser Gly Ala Leu Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575
```

-continued

Met Ser Tyr Val Met Cys Thr Gly Ser Phe Lys Leu Glu Lys Glu Val
580 585 590

Ala Glu Thr Gln His Gly Thr Val Leu Val Gln Val Lys Tyr Glu Gly
595 600 605

Thr Asp Ala Pro Cys Lys Ile Pro Phe Ser Thr Gln Asp Glu Lys Gly
610 615 620

Ala Thr Gln Asn Gly Arg Leu Ile Thr Ala Asn Pro Ile Val Thr Asp
625 630 635 640

Lys Glu Lys Pro Val Asn Ile Glu Ala Glu Pro Pro Phe Gly Glu Ser
645 650 655

Tyr Ile Val Val Gly Ala Gly Glu Lys Ala Leu Lys Leu Ser Trp Phe
660 665 670

Lys Lys Gly Ser Ser Ile Gly Lys Met Phe Glu Ala Thr Ala Arg Gly
675 680 685

Ala Arg Arg Met Ala Ile Leu Gly Asp Thr Ala Trp Asp Phe Gly Ser
690 695 700

Ile Gly Gly Val Phe Thr Ser Met Gly Lys Leu Val His Gln Val Phe
705 710 715 720

Gly Thr Ala Tyr Gly Val Leu Phe Ser Gly Val Ser Trp Thr Met Lys
725 730 735

Ile Gly Ile Gly Ile Leu Leu Thr Trp Leu Gly Leu Asn Ser Arg Asn
740 745 750

Thr Ser Leu Ser Val Met Cys Ile Ala Val Gly Met Val Thr Leu Tyr
755 760 765

Leu Gly Val Met Val Gln Ala Asp Ser Gly Cys Val Ile Asn Trp Lys
770 775 780

Gly Arg Glu Leu Lys Cys Gly Ser Gly Ile Phe Val Thr Asn Glu Val
785 790 795 800

His Thr Trp Thr Glu Gln Tyr Lys Phe Gln Ala Asp Ser Pro Lys Arg
805 810 815

Leu Ser Ala Ala Ile Gly Lys Ala Trp Glu Glu Gly Val Cys Gly Ile
820 825 830

Arg Ser Ala Thr Arg Leu Glu Asn Ile Met Trp Lys Gln Ile Ser Asn
835 840 845

Glu Leu Asn His Ile Leu Leu Glu Asn Asp Met Lys Phe Thr Val Val
850 855 860

Val Gly Asp Val Ser Gly Ile Leu Ala Gln Gly Lys Lys Met Ile Arg
865 870 875 880

Pro Gln Pro Met Glu His Lys Tyr Ser Trp Lys Ser Trp Gly Lys Ala
885 890 895

Lys Ile Ile Gly Ala Asp Val Gln Asn Thr Thr Phe Ile Ile Asp Gly
900 905 910

Pro Asn Thr Pro Glu Cys Pro Asp Asn Gln Arg Ala Trp Asn Ile Trp
915 920 925

Glu Val Glu Asp Tyr Gly Phe Gly Ile Phe Thr Thr Asn Ile Trp Leu
930 935 940

Lys Leu Arg Asp Ser Tyr Thr Gln Val Cys Asp His Arg Leu Met Ser
945 950 955 960

Ala Ala Ile Lys Asp Ser Lys Ala Val His Ala Asp Met Gly Tyr Trp
965 970 975

Ile Glu Ser Glu Lys Asn Glu Thr Trp Lys Leu Ala Arg Ala Ser Phe
980 985 990

Ile Glu Val Lys Thr Cys Ile Trp Pro Lys Ser His Thr Leu Trp Ser
995 1000 1005

-continued

```
Asn Gly  Val Leu Glu Ser Glu  Met Ile Ile Pro Lys  Ile Tyr Gly
    1010                 1015                 1020

Gly Pro  Ile Ser Gln His Asn  Tyr Arg Pro Gly Tyr  Phe Thr Gln
    1025                 1030                 1035

Thr Ala  Gly Pro Trp His Leu  Gly Lys Leu Glu Leu  Asp Phe Asp
    1040                 1045                 1050

Phe Cys  Glu Gly Thr Thr Val  Val Val Asp Glu His  Cys Gly Asn
    1055                 1060                 1065

Arg Gly  Pro Ser Leu Arg Thr  Thr Thr Val Thr Gly  Lys Ile Ile
    1070                 1075                 1080

His Glu  Trp Cys Cys Arg Ser  Cys Thr Leu Pro Pro  Leu Arg Phe
    1085                 1090                 1095

Lys Gly  Glu Asp Gly Cys Trp  Tyr Gly Met Glu Ile  Arg Pro Val
    1100                 1105                 1110

Lys Asp  Lys Glu Glu Asn Leu  Val Lys Ser Met Val  Ser Ala Gly
    1115                 1120                 1125

Ser Gly  Glu Val Asp Ser Phe  Ser Leu Gly Leu Leu  Cys Ile Ser
    1130                 1135                 1140

Ile Met  Ile Glu Glu Val Met  Arg Ser Arg Trp Ser  Lys Lys Met
    1145                 1150                 1155

Leu Met  Thr Gly Thr Leu Ala  Val Phe Leu Leu Leu  Ile Met Gly
    1160                 1165                 1170

Gln Leu  Thr Trp Ser Asp Leu  Ile Arg Leu Cys Ile  Met Val Gly
    1175                 1180                 1185

Ala Asn  Ala Ser Asp Lys Met  Gly Met Gly Thr Thr  Tyr Leu Ala
    1190                 1195                 1200

Leu Met  Ala Thr Phe Lys Met  Arg Pro Met Phe Ala  Val Gly Leu
    1205                 1210                 1215

Leu Phe  Arg Arg Leu Thr Ser  Arg Glu Val Leu Leu  Leu Thr Ile
    1220                 1225                 1230

Gly Leu  Ser Leu Val Ala Ser  Val Glu Leu Pro Ser  Ser Leu Glu
    1235                 1240                 1245

Glu Leu  Gly Asp Gly Leu Ala  Ile Gly Ile Met Met  Leu Lys Leu
    1250                 1255                 1260

Leu Thr  Asp Phe Gln Ser His  Gln Leu Trp Ala Thr  Leu Leu Ser
    1265                 1270                 1275

Leu Thr  Phe Ile Lys Thr Thr  Phe Ser Leu His Tyr  Ala Trp Lys
    1280                 1285                 1290

Thr Met  Ala Met Val Leu Ser  Ile Val Ser Leu Phe  Pro Leu Cys
    1295                 1300                 1305

Leu Ser  Thr Thr Ser Gln Lys  Thr Thr Trp Leu Pro  Val Leu Leu
    1310                 1315                 1320

Gly Ser  Leu Gly Cys Lys Pro  Leu Pro Met Phe Leu  Ile Thr Glu
    1325                 1330                 1335

Asn Lys  Ile Trp Gly Arg Lys  Ser Trp Pro Leu Asn  Glu Gly Ile
    1340                 1345                 1350

Met Ala  Val Gly Ile Val Ser  Ile Leu Leu Ser Ser  Leu Leu Lys
    1355                 1360                 1365

Asn Asp  Val Pro Leu Ala Gly  Pro Leu Ile Ala Gly  Gly Met Leu
    1370                 1375                 1380

Ile Ala  Cys Tyr Val Ile Ser  Gly Ser Ser Ala Asp  Leu Ser Leu
    1385                 1390                 1395

Glu Lys  Ala Ala Glu Val Ser  Trp Glu Glu Glu Ala  Glu His Ser
    1400                 1405                 1410
```

```
Gly Ala Ser His Asn Ile Leu Val Glu Val Gln Asp Asp Gly Thr
    1415                1420                1425

Met Lys Ile Lys Asp Glu Glu Arg Asp Asp Thr Leu Thr Ile Leu
    1430                1435                1440

Leu Lys Ala Thr Leu Leu Ala Val Ser Gly Val Tyr Pro Met Ser
    1445                1450                1455

Ile Pro Ala Thr Leu Phe Val Trp Tyr Phe Trp Gln Lys Lys Lys
    1460                1465                1470

Gln Arg Ser Gly Val Leu Trp Asp Thr Pro Ser Pro Pro Glu Val
    1475                1480                1485

Glu Arg Ala Val Leu Asp Asp Gly Ile Tyr Arg Ile Leu Gln Arg
    1490                1495                1500

Gly Leu Leu Gly Arg Ser Gln Val Gly Val Gly Val Phe Gln Glu
    1505                1510                1515

Gly Val Phe His Thr Met Trp His Val Thr Arg Gly Ala Val Leu
    1520                1525                1530

Met Tyr Gln Gly Lys Arg Leu Glu Pro Ser Trp Ala Ser Val Lys
    1535                1540                1545

Lys Asp Leu Ile Ser Tyr Gly Gly Gly Trp Arg Phe Gln Gly Ser
    1550                1555                1560

Trp Asn Thr Gly Glu Glu Val Gln Val Ile Ala Val Glu Pro Gly
    1565                1570                1575

Lys Asn Pro Lys Asn Val Gln Thr Thr Pro Gly Thr Phe Lys Thr
    1580                1585                1590

Pro Glu Gly Glu Val Gly Ala Ile Ala Leu Asp Phe Lys Pro Gly
    1595                1600                1605

Thr Ser Gly Ser Pro Ile Val Asn Arg Glu Gly Lys Ile Val Gly
    1610                1615                1620

Leu Tyr Gly Asn Gly Val Val Thr Thr Ser Gly Thr Tyr Val Ser
    1625                1630                1635

Ala Ile Ala Gln Ala Lys Ala Ser Gln Glu Gly Pro Leu Pro Glu
    1640                1645                1650

Ile Glu Asp Lys Val Phe Arg Lys Arg Asn Leu Thr Ile Met Asp
    1655                1660                1665

Leu His Pro Gly Ser Gly Lys Thr Arg Arg Tyr Leu Pro Ala Ile
    1670                1675                1680

Val Arg Glu Ala Ile Lys Arg Lys Leu Arg Thr Leu Ile Leu Ala
    1685                1690                1695

Pro Thr Arg Val Val Ala Ser Glu Met Ala Glu Ala Leu Lys Gly
    1700                1705                1710

Val Pro Ile Arg Tyr Gln Thr Thr Ala Val Lys Ser Glu His Thr
    1715                1720                1725

Gly Lys Glu Ile Val Asp Leu Met Cys His Ala Thr Phe Thr Met
    1730                1735                1740

Arg Leu Leu Ser Pro Val Arg Val Pro Asn Tyr Asn Met Ile Ile
    1745                1750                1755

Met Asp Glu Ala His Phe Thr Asp Pro Ala Ser Ile Ala Ala Arg
    1760                1765                1770

Gly Tyr Ile Ser Thr Arg Val Gly Met Gly Glu Ala Ala Ala Ile
    1775                1780                1785

Phe Met Thr Ala Thr Pro Pro Gly Ser Val Glu Ala Phe Pro Gln
    1790                1795                1800

Ser Asn Ala Ile Ile Gln Asp Glu Glu Arg Asp Ile Pro Glu Arg
    1805                1810                1815
```

-continued

```
Ser Trp  Asn Ser Gly Tyr Asp  Trp Ile Thr Asp Phe  Pro Gly Lys
    1820                 1825                 1830

Thr Val  Trp Phe Val Pro Ser  Ile Lys Ser Gly Asn  Asp Ile Ala
    1835                 1840                 1845

Asn Cys  Leu Arg Lys Asn Gly  Lys Arg Val Ile Gln  Leu Ser Arg
    1850                 1855                 1860

Lys Thr  Phe Asp Thr Glu Tyr  Gln Lys Thr Lys Asn  Asn Asp Trp
    1865                 1870                 1875

Asp Tyr  Val Val Thr Thr Asp  Ile Ser Glu Met Gly  Ala Asn Phe
    1880                 1885                 1890

Arg Ala  Asp Arg Val Ile Asp  Pro Arg Arg Cys Leu  Lys Pro Val
    1895                 1900                 1905

Ile Leu  Lys Asp Gly Pro Glu  Arg Val Ile Leu Ala  Gly Pro Met
    1910                 1915                 1920

Pro Val  Thr Val Ala Ser Ala  Ala Gln Arg Arg Gly  Arg Ile Gly
    1925                 1930                 1935

Arg Asn  Gln Asn Lys Glu Gly  Asp Gln Tyr Ile Tyr  Met Gly Gln
    1940                 1945                 1950

Pro Leu  Lys Asn Asp Glu Asp  His Ala His Trp Thr  Glu Ala Lys
    1955                 1960                 1965

Met Leu  Leu Asp Asn Ile Asn  Thr Pro Glu Gly Ile  Ile Pro Ala
    1970                 1975                 1980

Leu Phe  Glu Pro Glu Arg Glu  Lys Ser Ala Ala Ile  Asp Gly Glu
    1985                 1990                 1995

Tyr Arg  Leu Arg Gly Glu Ala  Arg Lys Thr Phe Val  Glu Leu Met
    2000                 2005                 2010

Arg Arg  Gly Asp Leu Pro Val  Trp Leu Ser Tyr Lys  Val Ala Ser
    2015                 2020                 2025

Glu Gly  Phe Gln Tyr Ser Asp  Arg Arg Trp Cys Phe  Asp Gly Glu
    2030                 2035                 2040

Arg Asn  Asn Gln Val Leu Glu  Glu Asn Met Asp Val  Glu Ile Trp
    2045                 2050                 2055

Thr Lys  Glu Gly Glu Arg Lys  Lys Leu Arg Pro Arg  Trp Leu Asp
    2060                 2065                 2070

Ala Arg  Thr Tyr Ser Asp Pro  Leu Ala Leu Arg Glu  Phe Lys Glu
    2075                 2080                 2085

Phe Ala  Ala Gly Arg Arg Ser  Val Ser Gly Asp Leu  Ile Leu Glu
    2090                 2095                 2100

Ile Gly  Lys Leu Pro Gln His  Leu Thr Gln Arg Ala  Gln Asn Ala
    2105                 2110                 2115

Leu Asp  Asn Leu Val Met Leu  His Asn Ser Glu Gln  Gly Gly Lys
    2120                 2125                 2130

Ala Tyr  Arg His Ala Met Glu  Glu Leu Pro Asp Thr  Ile Glu Thr
    2135                 2140                 2145

Leu Met  Leu Leu Ala Leu Ile  Ala Val Leu Thr Gly  Gly Val Thr
    2150                 2155                 2160

Leu Phe  Phe Leu Ser Gly Arg  Gly Leu Gly Lys Thr  Ser Ile Gly
    2165                 2170                 2175

Leu Leu  Cys Val Met Ala Ser  Ser Ala Leu Leu Trp  Met Ala Ser
    2180                 2185                 2190

Val Glu  Pro His Trp Ile Ala  Ala Ser Ile Ile Leu  Glu Phe Phe
    2195                 2200                 2205

Leu Met  Val Leu Leu Ile Pro  Glu Pro Asp Arg Gln  Arg Thr Pro
    2210                 2215                 2220
```

-continued

```
Gln Asp  Asn Gln Leu Ala Tyr  Val Val Ile Gly Leu  Leu Phe Val
    2225                 2230                 2235

Ile Leu  Thr Val Ala Ala Asn  Glu Met Gly Leu Leu  Glu Thr Thr
    2240                 2245                 2250

Lys Lys  Asp Leu Gly Ile Gly  His Val Ala Ala Glu  Asn His His
    2255                 2260                 2265

His Ala  Thr Met Leu Asp Val  Asp Leu His Pro Ala  Ser Ala Trp
    2270                 2275                 2280

Thr Leu  Tyr Ala Val Ala Thr  Thr Ile Ile Thr Pro  Met Met Arg
    2285                 2290                 2295

His Thr  Ile Glu Asn Thr Thr  Ala Asn Ile Ser Leu  Thr Ala Ile
    2300                 2305                 2310

Ala Asn  Gln Ala Ala Ile Leu  Met Gly Leu Asp Lys  Gly Trp Pro
    2315                 2320                 2325

Ile Ser  Lys Met Asp Ile Gly  Val Pro Leu Leu Ala  Leu Gly Cys
    2330                 2335                 2340

Tyr Ser  Gln Val Asn Pro Leu  Thr Leu Ile Ala Ala  Val Leu Met
    2345                 2350                 2355

Leu Val  Ala His Tyr Ala Ile  Ile Gly Pro Gly Leu  Gln Ala Lys
    2360                 2365                 2370

Ala Thr  Arg Glu Ala Gln Lys  Arg Thr Ala Ala Gly  Ile Met Lys
    2375                 2380                 2385

Asn Pro  Thr Val Asp Gly Ile  Val Ala Ile Asp Leu  Asp Pro Val
    2390                 2395                 2400

Val Tyr  Asp Ala Lys Phe Glu  Lys Gln Leu Gly Gln  Ile Met Leu
    2405                 2410                 2415

Leu Ile  Leu Cys Thr Ser Gln  Ile Leu Leu Met Arg  Thr Thr Trp
    2420                 2425                 2430

Ala Leu  Cys Glu Ser Ile Thr  Leu Ala Thr Gly Pro  Leu Thr Thr
    2435                 2440                 2445

Leu Trp  Glu Gly Ser Pro Gly  Lys Phe Trp Asn Thr  Thr Ile Ala
    2450                 2455                 2460

Val Ser  Met Ala Asn Ile Phe  Arg Gly Ser Tyr Leu  Ala Gly Ala
    2465                 2470                 2475

Gly Leu  Ala Phe Ser Leu Met  Lys Ser Leu Gly Gly  Gly Arg Arg
    2480                 2485                 2490

Gly Thr  Gly Ala Gln Gly Glu  Thr Leu Gly Glu Lys  Trp Lys Arg
    2495                 2500                 2505

Gln Leu  Asn Gln Leu Ser Lys  Ser Glu Phe Asn Thr  Tyr Lys Arg
    2510                 2515                 2520

Ser Gly  Ile Met Glu Val Asp  Arg Ser Glu Ala Lys  Glu Gly Leu
    2525                 2530                 2535

Lys Arg  Gly Glu Thr Thr Lys  His Ala Val Ser Arg  Gly Thr Ala
    2540                 2545                 2550

Lys Leu  Arg Trp Phe Val Glu  Arg Asn Leu Val Lys  Pro Glu Gly
    2555                 2560                 2565

Lys Val  Ile Asp Leu Gly Cys  Gly Arg Gly Gly Trp  Ser Tyr Tyr
    2570                 2575                 2580

Cys Ala  Gly Leu Lys Lys Val  Thr Glu Val Lys Gly  Tyr Thr Lys
    2585                 2590                 2595

Gly Gly  Pro Gly His Glu Glu  Pro Ile Pro Met Ala  Thr Tyr Gly
    2600                 2605                 2610

Trp Asn  Leu Val Arg Leu His  Ser Gly Lys Asp Val  Phe Phe Ile
    2615                 2620                 2625
```

-continued

```
Pro Pro  Glu Lys Cys Asp Thr  Leu Leu Cys Asp Ile  Gly Glu Ser
    2630                 2635                 2640

Ser Pro  Asn Pro Thr Ile Glu  Glu Gly Arg Thr Leu  Arg Val Leu
    2645                 2650                 2655

Lys Met  Val Glu Pro Trp Leu  Arg Gly Asn Gln Phe  Cys Ile Lys
    2660                 2665                 2670

Ile Leu  Asn Pro Tyr Met Pro  Ser Val Val Glu Thr  Leu Glu Gln
    2675                 2680                 2685

Met Gln  Arg Lys His Gly Gly  Met Leu Val Arg Asn  Pro Leu Ser
    2690                 2695                 2700

Arg Asn  Ser Thr His Glu Met  Tyr Trp Val Ser Cys  Gly Thr Gly
    2705                 2710                 2715

Asn Ile  Val Ser Ala Val Asn  Met Thr Ser Arg Met  Leu Leu Asn
    2720                 2725                 2730

Arg Phe  Thr Met Ala His Arg  Lys Pro Thr Tyr Glu  Arg Asp Val
    2735                 2740                 2745

Asp Leu  Gly Ala Gly Thr Arg  His Val Ala Val Glu  Pro Glu Val
    2750                 2755                 2760

Ala Asn  Leu Asp Ile Ile Gly  Gln Arg Ile Glu Asn  Ile Lys Asn
    2765                 2770                 2775

Glu His  Lys Ser Thr Trp His  Tyr Asp Glu Asp Asn  Pro Tyr Lys
    2780                 2785                 2790

Thr Trp  Ala Tyr His Gly Ser  Tyr Glu Val Lys Pro  Ser Gly Ser
    2795                 2800                 2805

Ala Ser  Ser Met Val Asn Gly  Val Val Arg Leu Leu  Thr Lys Pro
    2810                 2815                 2820

Trp Asp  Val Ile Pro Met Val  Thr Gln Ile Ala Met  Thr Asp Thr
    2825                 2830                 2835

Thr Pro  Phe Gly Gln Gln Arg  Val Phe Lys Glu Lys  Val Asp Thr
    2840                 2845                 2850

Arg Thr  Pro Lys Ala Lys Arg  Gly Thr Ala Gln Ile  Met Glu Val
    2855                 2860                 2865

Thr Ala  Arg Trp Leu Trp Gly  Phe Leu Ser Arg Asn  Lys Lys Pro
    2870                 2875                 2880

Arg Ile  Cys Thr Arg Glu Glu  Phe Thr Arg Lys Val  Arg Ser Asn
    2885                 2890                 2895

Ala Ala  Ile Gly Ala Val Phe  Val Asp Glu Asn Gln  Trp Asn Ser
    2900                 2905                 2910

Ala Lys  Glu Ala Val Glu Asp  Glu Arg Phe Trp Glu  Leu Val His
    2915                 2920                 2925

Arg Glu  Arg Glu Leu His Lys  Gln Gly Lys Cys Ala  Thr Cys Val
    2930                 2935                 2940

Tyr Asn  Met Met Gly Lys Arg  Glu Lys Lys Leu Gly  Glu Phe Gly
    2945                 2950                 2955

Lys Ala  Lys Gly Ser Arg Ala  Ile Trp Tyr Met Trp  Leu Gly Ala
    2960                 2965                 2970

Arg Phe  Leu Glu Phe Glu Ala  Leu Gly Phe Met Asn  Glu Asp His
    2975                 2980                 2985

Trp Phe  Ser Arg Glu Asn Ser  Leu Ser Gly Val Glu  Gly Glu Gly
    2990                 2995                 3000

Leu His  Lys Leu Gly Tyr Ile  Leu Arg Asp Ile Ser  Arg Ile Pro
    3005                 3010                 3015

Gly Gly  Asn Met Tyr Ala Asp  Asp Thr Ala Gly Trp  Asp Thr Arg
    3020                 3025                 3030
```

```
Ile Thr  Glu Asp Asp Leu Gln  Asn Glu Ala Lys Ile  Thr Asp Ile
    3035                 3040                 3045

Met Glu  Pro Glu His Ala Leu  Leu Ala Thr Ser Ile  Phe Lys Leu
    3050                 3055                 3060

Thr Tyr  Gln Asn Lys Val Val  Arg Val Gln Arg Pro  Ala Lys Asn
    3065                 3070                 3075

Gly Thr  Val Met Asp Val Ile  Ser Arg Arg Asp Gln  Arg Gly Ser
    3080                 3085                 3090

Gly Gln  Val Gly Thr Tyr Gly  Leu Asn Thr Phe Thr  Asn Met Glu
    3095                 3100                 3105

Ala Gln  Leu Ile Arg Gln Met  Glu Ser Glu Gly Ile  Phe Leu Pro
    3110                 3115                 3120

Ser Glu  Leu Glu Thr Pro Asn  Leu Ala Gly Arg Val  Leu Asp Trp
    3125                 3130                 3135

Leu Glu  Lys Tyr Gly Val Glu  Arg Leu Lys Arg Met  Ala Ile Ser
    3140                 3145                 3150

Gly Asp  Asp Cys Val Val Lys  Pro Ile Asp Asp Arg  Phe Ala Thr
    3155                 3160                 3165

Ala Leu  Thr Ala Leu Asn Asp  Met Gly Lys Val Arg  Lys Asp Ile
    3170                 3175                 3180

Pro Gln  Trp Glu Pro Ser Lys  Gly Trp Asn Asp Trp  Gln Gln Val
    3185                 3190                 3195

Pro Phe  Cys Ser His His Phe  His Gln Leu Ile Met  Lys Asp Gly
    3200                 3205                 3210

Arg Glu  Ile Val Val Pro Cys  Arg Asn Gln Asp Glu  Leu Val Gly
    3215                 3220                 3225

Arg Ala  Arg Val Ser Gln Gly  Ala Gly Trp Ser Leu  Arg Glu Thr
    3230                 3235                 3240

Ala Cys  Leu Gly Lys Ser Tyr  Ala Gln Met Trp Gln  Leu Met Tyr
    3245                 3250                 3255

Phe His  Arg Arg Asp Leu Arg  Leu Ala Ala Asn Ala  Ile Cys Ser
    3260                 3265                 3270

Ala Val  Pro Val Asp Trp Val  Pro Thr Ser Arg Thr  Thr Trp Ser
    3275                 3280                 3285

Ile His  Ala His His Gln Trp  Met Thr Thr Glu Asp  Met Leu Ser
    3290                 3295                 3300

Val Trp  Asn Arg Val Trp Ile  Glu Glu Asn Pro Trp  Met Glu Asp
    3305                 3310                 3315

Lys Thr  His Val Ser Ser Trp  Glu Glu Val Pro Tyr  Leu Gly Lys
    3320                 3325                 3330

Arg Glu  Asp Gln Trp Cys Gly  Ser Leu Ile Gly Leu  Thr Ala Arg
    3335                 3340                 3345

Ala Thr  Trp Ala Thr Asn Ile  Gln Val Ala Ile Asn  Gln Val Arg
    3350                 3355                 3360

Arg Leu  Ile Gly Asn Glu Asn  Tyr Leu Asp Tyr Met  Thr Ser Met
    3365                 3370                 3375

Lys Arg  Phe Lys Asn Glu Ser  Asp Pro Glu Gly Ala  Leu Trp
    3380                 3385                 3390
```

<210> SEQ ID NO 42
<211> LENGTH: 10723
<212> TYPE: DNA
<213> ORGANISM: Dengue virus -continued
<220> FEATURE:
<221> NAME/KEY: misc_feature
<222> LOCATION: (1)..(10723)
<223> OTHER INFORMATION: LAV2

<400> SEQUENCE: 42
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acacgaactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagag 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaagc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgtcatcagg aaacttactc ttcacaggac atctcaagtg caggctgaga 1800
atggacaagc tacagctcaa aggaatgtca tactctatgt gcacaggaaa gtttaaagtt 1860
gtgaaggaaa tagcagaaac acaacatgga acaatagtta tcagagtgca atatgaaggg 1920
gacggctctc catgcaagat cccttttgag ataatggatt tggaaaaaag acatgtctta 1980
ggtcgcctga ttacagtcaa cccaattgtg acagaaaaag atagcccagt caacatagaa 2040
gcagaacctc catttggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt gggaggagtg 2220

-continued

```
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
```

-continued

```
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgw gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
```

-continued

```
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
```

caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 43
<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 43
agttgttagt ctacgtggac cgacaagaac agtttcgact cggaagcttg cttaacgtag 60
tgctgacagt tttttattag agagcagatc tctgatgaac aaccaacgga aaaagacggg 120
aaaaccgtct atcaatatgc tgaaacgcgt gagaaaccgt gtgtcaactg gatcacagtt 180
ggcgaagaga ttctcaagag gattgctgaa cggccaagga ccaatgaaat tggttatggc 240
atttatagct ttcctcagat ttctagccat tccaccgaca gcaggagtct tggctagatg 300
gggtaccttt aagaagtcgg gggctattaa ggtcttaaaa ggcttcaaga aggagatctc 360
aaacatgctg agcattatca acaaacggaa aaagacatcg ctctgtctca tgatgatgtt 420
accagcaaca cttgctttcc acttaacttc acgagatgga gagccgcgca tgattgtggg 480
gaagaatgaa agaggaaaat ccctactttt caagacagcc tctggaatca acatgtgcac 540
actcatagct atggatctgg gagagatgtg tgatgacacg gtcacttaca aatgccccca 600
cattaccgaa gtggagcctg aagacattga ctgctggtgc aaccttacat cgacatgggt 660
gacttatgga acatgcaatc aagctggaga gcatagacgc gataagagat cagtggcgtt 720

-continued

```
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca aatacaccgt catcatcaca gtgcacacag gagaccaaca   1380
ccaggtggga aatgaaacgc agggagtcac ggctgagata acaccccagg catcaaccgc   1440
tgaagccatt ttacctgaat atggaaccct cgggctagaa tgctcaccac ggacaggttt   1500
ggatttcaat gaaatgatct yattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaagggatga gctatgcaat gtgcttgggt agctttgtgt tgaagaaaga   1860
agtctccgaa acgcagcatg ggacaatact cattaaggtt gagtacaaag ggaaagatgc   1920
accctgcaag attcctttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggct actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
```

-continued

```
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccactcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accacttttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
gggggttgga gtacagaaag aaggagtttt ccacaccatg tggcatgtca caagaggggc   4680
agtgttgaca cacaatggga aaagactgga accaaactgg gctagcgtga aaaaagatct   4740
gatttcatac ggaggaggat ggagattgag tgcacaatgg aaaaaggggg aggaggtgca   4800
ggttattgcc gtagagcctg ggaagaaccc aaagaacttt caaaccatgc caggcatttt   4860
tcagacaaca acaggggaaa taggagcaat tgcactggat ttcaagcctg gaacttcagg   4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
```

-continued agagagagac ataccggaac gctcatggaa ttcaggcaat gaatggatta ctgactttgt 5580
tgggaagaca gtgtggtttg tccctagcat caaagccgga aatgacatag caaactgctt 5640
gcggaaaaat ggaaaaaagg ttattcaact cagcaggaag acctttgaca cagaatatca 5700
aaagaccaaa ctgaatgatt gggactttgt ggtgacaaca gacatttcag aaatgggagc 5760
caatttcaaa gcagatagag tgatcgaccc aagaagatgt ctcaagccgg tgattttgac 5820
agatggaccc gagcgggtga tcctggctgg accaatgcca gtcaccgtag cgagcgctgc 5880
gcaaaggaga gggagagttg gcaggaaccc acaaaaagaa aatgaccagt acatattcat 5940
gggccagcct ctcaacaatg atgaagacca tgctcactgg acagaagcaa aaatgctgct 6000
ggacaacatc aacacaccag aagggattat accagctctc tttgaaccag aaagggagaa 6060
gtcagccgcc atagacggcg aataccgcct gaagggtgag tccaggaaga ctttcgtgga 6120
actcatgagg aggggtgacc tcccagtttg gctagcccat aaagtagcat cagaagggat 6180
caaatataca gatagaaaat ggtgctttga tggagaacgt aataatcaaa ttttagagga 6240
gaatatggat gtggaaatct ggacaaagga aggagaaaag aaaaaactga gacctaggtg 6300
gcttgatgcc cgcacttatt cagatccttt agcactcaaa gaattcaagg attttgcagc 6360
tggcagaaag tcaatcgccc ttgatcttgt gacagaaata ggaagagtgc cttcacactt 6420
agcccacaga acgagaaacg ccctggataa tttggtgatg ctgcacacgt cagaacatgg 6480
cggtagggcc tacaggcatg cagtggagga actaccagaa acgatggaaa cactcttact 6540
cctgggactg atgatcttgt taacaggtgg agcaatgctc ttcttgatat caggtaaagg 6600
gattggaaag acttcaatag gactcatttg tgtaattgct tccagcggca tgttatggat 6660
ggctgatgtc ccactccaat ggatcgcatc ggctatagtc ctggagtttt ttatgatggt 6720
gttgctcata ccagaaccag aaaagcagag aactccccaa gacaaccaac tcgcatatgt 6780
cgtgataggc atacttacat tggctgcaat agtagcggcc aatgaaatgg gactgttgga 6840
aactacaaag agagatttag gaatgtctaa agaaccaggt gttgtttctc caaccagcta 6900
tttggatgtg gacttgcacc cagcatcagc ctggacattg tacgccgtgg ccacaacagt 6960
aataacacca atgttgagac acaccataga gaattccaca gcaaatgtgt ctctggcagc 7020
catagctaac caggcagtgg tcctgatggg tttagacaaa ggatggccga tatcgaaaat 7080
ggacttgggc gtaccactat tggcactggg ttgctattca caagtgaacc cactaactct 7140
tgcagcggca gtacttttgc tagtcacaca ttatgcaatt ataggtccag gattgcaggc 7200
aaaagccacc cgtgaagctc agaaaaggac agctgctgga ataatgaaga atccaacggt 7260
ggatggaata atgacaatag acctagatcc tgtaatatat gattcaaaat ttgaaaagca 7320
actaggacag gtcatgctcc tggttctgtg tgcagtccaa cttttattga tgagaacatc 7380
atgggccttg tgtgaagttc taaccctagc cacaggacca ataacaacac tctgggaagg 7440
atcacctggg aagttctgga acaccacgat agctgtttcc atggcgaaca tctttagagg 7500
gagctattta gcaggagctg ggcttgcttt ttctatcatg aaatcagttg gaacaggaaa 7560
gagaggaaca gggtcacaag gtgaaacctt aggagaaaag tggaaaaaga aattaaatca 7620
gttatcccgg aaagagtttg acctttacaa gaaatccgga atcaccgaag tggatagaac 7680
agaagccaaa gaagggttaa aaagaggaga aataacacac catgccgtgt ccagaggcag 7740
cgcaaaactt caatggttcg tggagagaaa catggtcatt cctgaaggaa gagtcataga 7800
cctaggctgt ggaagaggag gctggtcata ttactgtgca ggactgaaaa aagttacaga 7860
agtgcgagga tacacaaaag gcggcccagg acacgaagaa ccagtaccta tgtctacata 7920

-continued

```
cggatggaac atagtcaagt taatgagtgg aaaggatgtt ttttatctgc cacctgaaaa   7980

gtgtgatacc ctattgtgtg acattggaga atcttcacca agcccaacag tggaagaaag   8040

cagaaccata agagttttga agatggttga accatggcta aagaacaacc agttttgcat   8100

taaagtattg aacccataca tgccaactgt gattgagcac ttagaaagac tacaaaggaa   8160

acatggagga atgcttgtga gaaatccact ctcacgaaac tccacgcacg aaatgtattg   8220

gatatccaat ggtacaggca atatcgtctc ttcagtcaac atggtatcca gattgctact   8280

gaacagattc acaatgacac acaggagacc caccatagag aaagatgtgg atctaggagc   8340

aggaacccga catgtcaatg cggaaccaga aacacccaac atggatgtca ttggggaaag   8400

aataaaaagg atcaaagagg agcatagttc aacatggcac tatgatgatg aaaatcctta   8460

caaaacgtgg gcttaccatg gatcctatga agtaaaagcc acaggctcag cctcctccat   8520

gataaatgga gtcgtgaaac tcctcacaaa accatgggat gtggtgccca tggtgacaca   8580

gatggcaatg acagatacaa ctccattcgg ccagcaaaga gtttttaaag agaaagtgga   8640

caccaggaca cctaggccca tgccaggaac aagaaaggtt atggagatca cagcggagtg   8700

gctttggagg accctgggaa ggaacaaaag acccagatta tgcacaaggg aggaattcac   8760

aaagaaggtc agaaccaacg cagctatggg cgctgtcttc acagaagaga accaatggga   8820

cagtgcgaga gctgctgttg aggacgaaga attttggaaa cttgtggaca gagaacgtga   8880

actccacaaa ctgggcaagt gtggaagctg cgtttacaac atgatgggca agagagagaa   8940

aaaacttgga gagtttggta aagcaaaagg cagtagggct atatggtaca tgtggttggg   9000

agccaggtac cttgagttcg aggcgctcgg attcctcaat gaagaccact ggttctcgcg   9060

tgaaaactct tacagtggag tagaaggaga aggactgcac aagctgggat acatcttgag   9120

agatatttcc aagatacccg gaggagccat gtatgctgat gacacagccg gttgggacac   9180

aagaataaca gaagatgacc tgcacaatga ggaaaaaatc acacagcaga tggaccctga   9240

acacaggcag ctagcgaacg ctatattcaa gctcacatac caaaacaaag tggtcaaagt   9300

ccaacgacca actccaaagg gcacggtaat ggacatcata tctaggaaag accaaagagg   9360

cagtggacag gtgggaactt atggtctgaa cacattcacc aacatggaag cccagctaat   9420

cagacaaatg gaaggagaag gcgtgttgtc aaaggcagac ctcgagaacc cccatccgct   9480

agagaagaaa attacacaat ggttggaaac taaaggagtg gaaaggttaa aaagaatggc   9540

catcagcggg gatgattgcg ttgtgaaacc aatcgacgac agattcgcca atgccctgct   9600

tgccctgaac gatatgggaa aggttagaaa ggacatacct caatggcagc catcaaaggg   9660

atggcatgat tggcaacagg tccccttctg ctcccaccac tttcatgaat tgatcatgaa   9720

agatggaaga aagttggtag ttccctgcag accccaggac gaactaatag gaagagcgag   9780

aatctcccaa ggagcaggat ggagccttag agaaactgca tgtctaggga aagcctacgc   9840

tcaaatgtgg gctctcatgt attttcacag aagagatctt agactagcat ccaacgccat   9900

atgttcagca gtaccagtcc actgggtccc cacgagcaga acgacatggt ctattcatgc   9960

tcaccatcag tggatgacta cagaagacat gcttactgtc tggaacaggg tgtggataga  10020

ggacaatcca tggatggaag acaaaactcc agtcacaacg tgggaagatg ttccatatct  10080

agggaagaga gaagaccaat ggtgcggatc actcataggt ctcacttcca gagcaacctg  10140

ggcccagaac atactcacag caatccaaca ggtgagaagc ctcataggca atgaagagtt  10200

tctggactac atgccttcga tgaagagatt caggaaggag gaggagtcag agggagccat  10260

ttggtaaaag caggaggtaa actgtcaggc cacattaagc cacagtacgg aagaagctgt  10320
```

gcagcctgtg agccccgtcc aaggacgtta aaagaagaag tcaggcccaa aagccacggt 10380
ttgagcaaac cgtgctgcct gtagctccgt cgtggggacg taaagcctgg gaggctgcaa 10440
accgtggaag ctgtacgcac ggtgtagcag actagtggtt agaggagacc cctcccatga 10500
cacaacgcag cagcggggcc cgagcactga gggaagctgt acctccttgc aaaggactag 10560
aggttagagg agacccccccg caaacaaaaa cagcatattg acgctgggag agaccagaga 10620
tcctgctgtc tcctcagcat cattccaggc acagaacgcc agaaaatgga atggtgctgt 10680
tgaatcaaca ggttctagt 10699

<210> SEQ ID NO 44
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

<400> SEQUENCE: 44
agttgttagt ctgtgtggac cgacaaggac agttccaaat cggaagcttg cttaacacag 60
ttctaacagt ttgtttgaat agagagcaga tctctggaaa aatgaaccaa cgaaaaaagg 120
tggttagacc acctttcaat atgctgaaac gcgagagaaa ccgcgtatca acccctcaag 180
ggttggtgaa gagattctca accggacttt tttctgggaa aggaccctta cggatggtgc 240
tagcattcat cacgtttttg cgagtccttt ccatccccacc aacagcaggg attctgaaaa 300
gatggggaca gttgaagaaa aataaggcca tcaggatact gattggattc aggaaggaga 360
taggccgcat gctgaacatc ttgaacggga gaaaaaggtc aacgataaca ttgctgtgct 420
tgattcccac cgtaatggcg tttcacttgt caacaagaga tggcgaaccc ctcatgatag 480
tggcaaaaca tgaaaggggg agacctctct tgtttaagac aacagagggg atcaacaaat 540
gcactctcat tgccatggac ttgggtgaaa tgtgtgagga cactgtcacg tataaatgcc 600
ccttactggt caataccgaa cctgaagaca ttgattgctg gtgcaatctc acgtctacct 660
gggtcatgta tgggacatgc acccagagcg gagaacggag acgagagaag cgctcagtag 720
ctttaacacc acattcagga atgggattgg aaacaagagc tgagacatgg atgtcatcgg 780
aaggggcttg gaagcatgct cagagagtag agagctggat actcagaaac ccaggattcg 840
cgctcttggc aggatttatg gcttatatga ttgggcaaac aggaatccag cgaactgtct 900
tctttgtcct aatgatgctg gtcgccccat cctacggaat gcgatgcgta ggagtaggaa 960
acagagactt tgtggaagga gtctcaggtg gagcatgggt cgatctggtg ctagaacatg 1020
gaggatgcgt cacaaccatg gcccagggaa aaccaacctt ggattttgaa ctgactaaga 1080
caacagccaa ggaagtggct ctgttaagaa cctattgcat tgaagcctca atatcaaaca 1140
taaccacggc aacaagatgt ccaacgcaag gagagcctta tctaaaagag gaacaagacc 1200
aacagtacat ctgccggaga gatgtggtag acagagggtg gggcaatggc tgtggcttgt 1260
ttggaaaagg aggagttgtg acatgtgcga agttttcatg ttcggggaag ataacaggca 1320
atttggtcca aattgagaac cttgaataca cagtggttgt aacagtccac aatggagaca 1380
cccatgcagt aggaaatgac acatccaatc atggagttac agccacgata actcccaggt 1440
caccatcggt ggaagtcaaa ttgccggact atggagaact aacactcgat tgtgaaccca 1500
ggtctggaat tgactttaat gagatgattc tgatgaaaat gaaaaagaaa acatggcttg 1560
tgcataagca atggtttttg gatctacctc taccatggac agcaggagca gacacatcag 1620

-continued

```
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatctcaag tgcaaagtcc   1800
gtatggagaa attgagaatc aagggaatgt catacacgat gtgttcagga aagttctcaa   1860
ttgacaaaga gatggcagaa acacagcatg ggacaacagt ggtgaaagtc aagtatgaag   1920
gtgctggagc tccgtgtaaa gtccccatag agataagaga tgtgaacaag aaaaaagtgg   1980
ttgggcgtat catctcatcc accccttttgg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggtttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
gggtctgtgg aattagatca accacgaggc tggaaaatgt catgtggaag caaataacca   2640
acgagctaaa ttatgttctc tgggaaggag gacatgacct cactgtagtg gctggggatg   2700
tgaagggggt gttgaccaaa ggcaagagag cactcacacc cccagtgaat gatctgaaat   2760
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acattgtgga   3120
gcaatggagt gctggaaagc cagatgctca ttccaaaatc atatgcgggc cctttttcac   3180
accacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct cccttaaggt tcttgggaga agatgggtgc tggtatggga   3420
tggagattag gcccttgagt gaaaaagaag agaacatggt caaatcacag gtaacggccg   3480
gacagggcac atcagaaact tttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctggggctaa ttttgctaaa aatagtgaca cattttgaca   3900
acacccaagt gggaacctta gccctttcct tgaccttcat aagatcaaca atgccattgg   3960
tcatggcttg gaggaccatt atggctgtgt tgtttgtggt cacactcatt cctttgtgca   4020
```

-continued

```
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg gcggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380
ctttctccat acgggacgtc gaggaaacca atatgataac ccttttggtg aaactggcac   4440
tgataacagt gtcaggtctc taccccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaaagaggg ttatttggga   4620
aaactcaggt tggagtaggg atacacatgg aaggtgtatt tcacacaatg tggcatgtaa   4680
caagaggatc agtgatctgc catgagactg ggagattgga gccatcttgg gctgacgtca   4740
ggaatgacat gatatcatac ggtgggggat ggagacttgg agacaaatgg gacaaagaag   4800
aagatgttca ggtcctcgcc atagaaccag gaaaaaatcc taaacatgtc caaacgaaac   4860
ccggcctttt caagacccta actggagaaa ttggagcagt aacattagat ttcaaacccg   4920
gaacgtctgg ttctcccatc atcaacagga aaggaaaagt catcggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
tacaccccgg agctggaaag acaaaaagaa ttcttccatc aatagtgaga gaagccttaa   5160
aaaggaggct gcgaaccttg attttggctc ccacgagagt ggtggcggcc gagatggaag   5220
aggccctacg tggactgcca atccgttatc agaccccagc tgtgaaatca gaacacacag   5280
gaagagagat tgtagacctc atgtgtcatg caaccttcac aacaagactt ttgtcatcaa   5340
ccagagttcc aaattacaac ctcatagtga tggatgaagc acatttcacc gatccttcta   5400
gtgtcgcggc tagaggatac atctcgacca gggtggaaat gggagaggca gcagccatct   5460
tcatgaccgc aacccctccc ggagcgacag atccctttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg attttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
```

-continued

```
cttacctttc ctctagggcc aagctcgccc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatgggtt tgataaccat tgcggtggct agtggcttgt   6660
tctgggtagc agaaattcaa ccccagtgga tagcggcctc aatcatacta gagtttttc    6720
tcatggtact gttgataccg gaaccagaaa aacaaaggac cccacaagac aatcaattga   6780
tctacgtcat attgaccatt ctcaccatta ttggtctcat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca ggcggccgtc ctaatggggc ttggaaaagg atggccgctc cacagaatgg   7080
acctcggtgt gccgctgtta gcaatgggat gctattctca agtgaaccca acaactttga   7140
cagcatcctt agtcatgctt tcagtccatt atgcaataat aggtccagga ttgcaggcaa   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacctggc gggagctgga ctggcttttt cactcataaa gaatgyacaa acccctagga   7560
ggggaactgg gaccacagga gagacactgg gagagaagtg gaagagacag ctaaactcat   7620
takacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg ggcgtatcat ggaagctatg aagctccttc gacaggctct gcatcctcca   8520
tggtgaacgg ggtagtaaaa ctgctaacaa aaccttggga tgtggttcca atggtgaccc   8580
agttagccat gacagacaca accccttttg ggcaacaaag agtgttcaaa gagaaggtgg   8640
ataccagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
```

-continued

```
catcagccag tgaagctgtg aatgacagcc ggttttggga actggttgac aaagaaaggg   8880
ccctacacca ggaagggaaa tgtgaatcgt gtgtctacaa catgatggga aaacgtgaga   8940
aaaagttagg agagtttggc agagccaagg gaagccgagc aatctggtac atgtggctgg   9000
gagcgcggtt tctggaattt gaagccctgg gtttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aagaactgat cacggaacag atggcccccc   9240
accacaagat cctagccaaa gccattttca aactaaccta tcaaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc ccctggatga gaggtttggc acttccctcc   9600
tcttcttgaa cgacatggga aaggtgagga aagacattcc gcagtgggaa ccatctaagg   9660
gatggaaaaa ctggcaagag gttccttttt gctcccacca ctttcacaag atcttcatga   9720
aggatggccg ctcactagtt gttccatgta gaaaccagga tgaactgata gggagagcca   9780
gaatctcgca gggggctgga tggagcttaa gagaaacagc ctgcctgggc aaagcttacg   9840
cccagatgtg gtcgctcatg tacttccaca gaagggatct gcgtttagcc tccatggcca   9900
tatgctcagc agttccaacg gaatggtttc caacaagcag aacaacatgg tcaatccacg   9960
ctcatcatca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcagaaa cctgatcgga aaagaggaat  10200
acgtggatta catgccagta atgaaaagat acagcgctcc ttcagagagt gaaggagttc  10260
tgtaattacc aacaacaaac accaaaggct attgaagtca ggccacttgt gccacggctt  10320
gagcaaaccg tgctgcctgt agctccgcca ataatgggag gcgtgaaatc cctagggagg  10380
ccatgcgcca cggaagctgt acgcgtggca tattggacta gcggttagag gagacccctc  10440
ccatcactga caaaacgcag caaaaggggg cccgaagcca ggaggaagct gtactcctgg  10500
tggaaggact agaggttaga ggagaccccc ccaacacaaa aacagcatat tgacgctggg  10560
aaagaccaga gatcctgctg tctctgcaac atcaatccag gcacagagcg aagcaagatg  10620
gattggtgtt gttgatccaa caggttct                                     10648
```